(12) United States Patent
Nakamura et al.

(10) Patent No.: US 8,420,572 B2
(45) Date of Patent: Apr. 16, 2013

(54) FUNGICIDAL COMPOSITION CONTAINING CARBOXYLIC ACID AMIDE DERIVATIVE

(75) Inventors: Yuji Nakamura, Kusatsu (JP); Shigeru Mitani, Kusatsu (JP); Shintaro Tsukuda, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 1117 days.

(21) Appl. No.: 12/095,517

(22) PCT Filed: Dec. 13, 2006

(86) PCT No.: PCT/JP2006/325320
§ 371 (c)(1),
(2), (4) Date: May 30, 2008

(87) PCT Pub. No.: WO2007/069777
PCT Pub. Date: Jun. 21, 2007

(65) Prior Publication Data
US 2010/0222337 A1     Sep. 2, 2010

(30) Foreign Application Priority Data

Dec. 16, 2005   (JP) ................................ 2005-363286
Sep. 20, 2006   (JP) ................................ 2006-254477

(51) Int. Cl.
*A01N 43/40*   (2006.01)
*A01N 25/00*   (2006.01)
*A61K 31/785*  (2006.01)

(52) U.S. Cl.
USPC ..... 504/244; 424/78.36; 424/405; 504/116.1; 504/130

(58) Field of Classification Search ............ 504/244, 504/116.1, 130; 424/78.36, 405
See application file for complete search history.

(56) References Cited

FOREIGN PATENT DOCUMENTS

| | | |
|---|---|---|
| EP | 0 170 498 | 2/1986 |
| EP | 0 430 127 | 6/1991 |
| EP | 1 256 569 A1 | 11/2002 |
| EP | 1 428 817 A1 | 6/2004 |
| JP | 2005 179234 | 7/2005 |
| WO | 2006 016708 | 2/2006 |
| WO | WO 2006/016708 A1 | 2/2006 |
| WO | 2007 006739 | 1/2007 |

OTHER PUBLICATIONS

U.S. Appl. No. 12/640,140, filed Dec. 17, 2009, Nakamura, et al.
U.S. Appl. No. 12/740,121, filed Apr. 28, 2010, Mitani, et al.
U.S. Appl. No. 12/822,204, filed Jun. 24, 2010, Nakamura, et al.
U.S. Appl. No. 12/822,206, filed Jun. 24, 2010, Nakamura, et al.

*Primary Examiner* — Mina Haghighatian
*Assistant Examiner* — Helen Chui
(74) *Attorney, Agent, or Firm* — Oblon, Spivak, McClelland, Maier & Neustadt, L.L.P.

(57) ABSTRACT

Conventional fungicidal compositions have had practical problems such that either a preventive effect or a curative effect is inadequate, the residual effect tends to be inadequate, or the controlling effect against plant diseases tends to be inadequate depending upon the application site, and a fungicidal composition to overcome such problems has been desired. The present invention provides a fungicidal composition containing a carboxylic acid amide derivative of the formula (I) or a salt thereof, as an active ingredient: wherein A is phenyl which may be substituted, benzodioxolanyl which may be substituted, or benzodioxanyl which may be substituted; B is 2- or 3-pyridyl which may be substituted; each of $R^1$ and $R^2$ is alkyl, or $R^1$ and $R^2$ may together form a 3- to 6-membered saturated carbon ring, provided that when B is 3-pyridyl which may be substituted, A is phenyl substituted by at least two substituents.

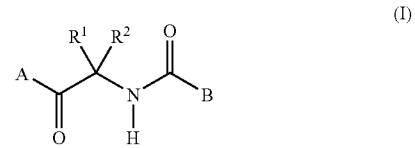

(I)

12 Claims, No Drawings

FUNGICIDAL COMPOSITION CONTAINING CARBOXYLIC ACID AMIDE DERIVATIVE

TECHNICAL FIELD

The present invention relates to a fungicidal composition containing a carboxylic acid amide derivative.

BACKGROUND ART

Patent Document 1 discloses that compounds of the after-mentioned formula (I) wherein A is phenyl having a certain substituent, and B is pyridyl having a certain substituent, are useful as active ingredients for pesticides, particularly for insecticides, miticides or nematicides. Further, Patent Document 2 discloses that some of such compounds have fungicidal activities, and it specifically discloses that such a compound wherein B is 3-fluoro-4-pyridyl i.e. 3-fluoro-N-(2-methyl-1-oxo-1-(4'-(trifluoromethoxy)biphenyl-4-yl)propan-2-yl)isonicotinamide is effective against sheath blight of rice. Further, Patent Document 3 discloses that compounds of the after-mentioned formula (I) wherein A is phenyl having a certain substituents or a condensed heterocyclic group having a certain substituent, and B is pyridyl having a certain substituent, are useful as active ingredients for pesticides, particularly for insecticides, miticides or nematicides. However, in these publications, compounds of the after-mentioned formula (I) are not specifically disclosed. On the other hand, Patent Document 4 discloses that compounds wherein. A is phenyl having a certain substituent or, a condensed heterocyclic group having a certain substituent, and B is a heterocyclic group having a certain substituent, have fungicidal activities, but pyridyl is not included in the heterocyclic group.

Patent Document 1: EP-A-1256569
Patent Document 2: JP-A-2005-179234
Patent Document 3: EP-A-1428817
Patent Document 4: WO06/016708

DISCLOSURE OF THE INVENTION

Conventional many fungicidal compositions have had practical problems such that either a preventive effect or a curative effect is inadequate, the residual effect tends to be inadequate, or the controlling effect against plant diseases tends to be inadequate depending upon the application methods. Accordingly, a fungicidal composition to overcome such problems has been desired.

The present inventors have conducted a research to solve the above problems and as a result, have found that compounds of the after-mentioned formula (I) wherein B is 2- or 3-pyridyl which may be substituted, exhibit excellent effects which are not observed in the prior art, i.e. preventive effects and curative effects against any of various diseases caused by noxious fungi such as Oomycetes, Ascomycetes, Basidiomycetes and Deuteromycetes, and at the same time, have practically satisfactory residual activities, and besides, they exhibit particularly excellent preventive effects and curative effects against various diseases caused by Ascomycetes or Deuteromycetes. The present invention has been accomplished on the basis of such a discovery.

Namely, the present invention provides a fungicidal composition containing a carboxylic acid amide derivative of the formula (I) or a salt thereof as an active ingredient:

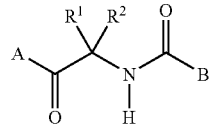

wherein A is phenyl which may be substituted by X, benzodioxolanyl which may be substituted by X, or benzodioxanyl which may be substituted by X; B is 2- or 3-pyridyl which may be substituted; each of $R^1$ and $R^2$ is alkyl, or $R^1$ and $R^2$ may together form a 3- to 6-membered saturated carbon ring; X is halogen, alkyl, haloalkyl, alkenyl, haloalkenyl, alkynyl, haloalkynyl, hydroxy, alkoxy, haloalkoxy, alkenyloxy, haloalkenyloxy, alkynyloxy, haloalkynyloxy, cycloalkyloxy, alkylthio, haloalkylthio, alkenylthio, haloalkenylthio, alkynylthio, haloalkynylthio, alkylsulfonyloxy, haloalkylsulfonyloxy, alkoxyalkoxy, haloalkoxyalkoxy, alkoxyhaloalkoxy, haloalkoxyhaloalkoxy, alkoxyalkyl, haloalkoxyalkyl, alkylthioalkyl, haloalkylthioalkyl, phenyl which may be substituted by Y, phenoxy which may be substituted by Y, benzyloxy which may be substituted Y, pyridyl which may be substituted by Y, or pyridyloxy which may be substituted by Y; and Y is halogen, alkyl, haloalkyl, alkenyl, haloalkenyl, alkynyl, haloalkynyl, alkoxy or haloalkoxy, provided that when B is 3-pyridyl which may be substituted, A is phenyl which is substituted by at least two X (such a plurality of X may be the same or different).

The present invention further provides a carboxylic acid amide derivative of the formula (I) or a salt thereof.

The present invention also provides a mixed fungicidal composition comprising a carboxylic acid amide derivative of the formula (I) or a salt thereof and another fungicidally active ingredient compound, as active ingredients.

Further, the present invention provides a method for controlling noxious fungi, which comprises applying an effective amount of a carboxylic acid amide derivative of the formula (I) or a salt thereof.

Still further, the present invention provides a method for controlling plant diseases, which comprises applying an effective amount of a carboxylic acid amide derivative of the formula (I) or a salt thereof.

Furthermore, the present invention provides a method for protecting crop plants, which comprises applying an effective amount of a carboxylic acid amide derivative of the formula (I) or a salt thereof.

Furthermore, the present invention provides a method for improving crop yields, which comprises applying an effective amount of a carboxylic acid amide derivative of the formula (I) or a salt thereof.

The fungicidal composition containing a carboxylic acid amide derivative of the formula (I) or a salt thereof as an active ingredient (hereinafter referred to simply as the composition of the present invention) is capable of effectively controlling noxious fungi, particularly Ascomycetes or Deuteromycetes, at a low dose and thus is useful as an agricultural or horticultural fungicidal composition.

BEST MODE FOR CARRYING OUT THE INVENTION

In A, the number of substituents X in the phenyl which may be substituted by X, the benzodioxolanyl which may be substituted by X and the benzodioxanyl which may be substituted by X, may be one or more, and in the case of more than one, such substituents may be the same or different. Further, their positions for substitution may be any positions.

In B, the substituent in the 2- or 3-pyridyl which may be substituted, may, for example, be halogen, alkyl, haloalkyl, alkoxy or haloalkoxy, and among them, halogen, alkyl or haloalkyl is preferred. The number of such substituents may be one or more, and in the case of more than one, such substituents may be the same or different. Further, their positions for substitution may be any positions. However, it preferably has a substituent at an ortho position to the aminocarbonyl moiety of the above formula (I). In such a case, it may have a substituent only at the ortho position to the aminocarbonyl moiety, or may have further substituents at other positions.

In X, the number of substituents Y in the phenyl which may be substituted by Y, the phenoxy which may be substituted by Y, the benzyloxy which may be substituted by Y, the pyridyl which may be substituted by Y, or the pyridyloxy which may be substituted by Y, may be one or more, and in the case of more than one, such substituents may be the same or different. Further, their positions for substitution may be any positions.

The number of halogen as substituents contained in X or Y may be one or more, and in the case of more than one, they may be the same or different. Further, their positions may be any positions.

An atom of fluorine, chlorine, bromine or iodine may be mentioned as a specific example of the halogen or halogen moiety contained in a substituent of the 2- or 3-pyridyl which may be substituted in B, or the halogen or halogen moiety contained in X or Y.

The alkyl or alkyl moiety contained in a substituent of the 2- or 3-pyridyl which may be substituted, in B, or the alkyl or alkyl moiety contained in $R^1$, $R^2$, X or Y may be linear or branched, and as a specific example thereof, $C_{1-12}$ alkyl may be mentioned such as methyl, ethyl, propyl, isopropyl, butyl, isobutyl, sec-butyl, tert-butyl, pentyl, isopentyl, neopentyl, tert-pentyl, 1-methylbutyl, hexyl, heptyl, octyl, nonyl, decanyl, undecanyl or dodecanyl.

The alkenyl or alkenyl moiety contained in X or Y may be linear or branched, and as a specific example thereof, $C_{2-6}$ alkenyl may be mentioned such as vinyl, 1-propenyl, allyl, isopropenyl, 1-butenyl, 1,3-butadienyl or 1-hexenyl.

The alkynyl or alkynyl moiety contained in X or Y may be linear or branched, and as a specific example thereof, $C_{2-6}$ alkynyl may be mentioned such as ethynyl, 2-butynyl, 2-pentynyl, 3-methyl-1-butynyl, 2-penten-4-ynyl, or 3-hexynyl.

As a specific example of the cycloalkyl moiety contained in X, $C_{3-6}$ cycloalkyl may be mentioned such as cyclopropyl, cyclobutyl, cyclopentyl or cyclohexyl.

The salt of the carboxylic acid amide derivative of the above formula (I) may be any salt so long as it is agriculturally acceptable. For example, it may be an alkali metal salt such as a sodium salt or a potassium salt; an alkaline earth metal salt such as a magnesium salt or a calcium salt; an amine salt such as a dimethylamine salt or a triethylamine salt; an inorganic acid salt such as a hydrochloride, a perchlorate, a sulfate or a nitrate; or an organic acid salt such as an acetate or a methane sulfonate.

The carboxylic acid amide derivative of the above formula (I) has various isomers such as optical isomers or geometrical isomers, and the present invention includes both isomers and mixtures of such isomers. Further, the present invention also includes various isomers other than the above isomers within the common knowledge in the technical field concerned. Further, depending upon the types of isomers, they may have chemical structures different from the above formula (I), but they are within the scope of the present invention, since it is obvious to those skilled in the art that they are isomers.

In the carboxylic acid amide derivative of the above formula (I), a carboxylic acid amide derivative of the formula (I-a) or a salt thereof:

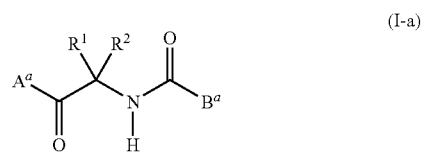

(I-a)

wherein $A^a$ is phenyl which may be substituted by X, $B^a$ is 2-pyridyl which may be substituted; each of $R^1$ and $R^2$ is alkyl, or $R^1$ and $R^2$ may together form a 3- to 6-membered saturated carbon ring; X is halogen, alkyl, haloalkyl, alkenyl, haloalkenyl, alkynyl, haloalkynyl, hydroxy, alkoxy, haloalkoxy, alkenyloxy, haloalkenyloxy, alkynyloxy, haloalkynyloxy, cycloalkyloxy, alkylthio, haloalkylthio, alkenylthio, haloalkenylthio, alkynylthio, haloalkynylthio, alkylsulfonyloxy, haloalkylsulfonyloxy, alkoxyalkoxy, haloalkoxyalkoxy, alkoxyhaloalkoxy, haloalkoxyhaloalkoxy, alkoxyalkyl, haloalkoxyalkyl, alkylthioalkyl, haloalkylthioalkyl, phenyl which may be substituted by Y, phenoxy which may be substituted by Y, benzyloxy which may be substituted by Y, pyridyl which may be substituted by Y, or pyridyloxy which may be substituted by Y; and Y is halogen, alkyl, haloalkyl, alkenyl, haloalkenyl, alkynyl, haloalkynyl, alkoxy or haloalkoxy, is a novel compound which has not heretofore been specifically known and is a compound which exhibits particularly excellent preventive effects and curative effects against various diseases caused by Ascomycetes or Deuteromycetes.

The carboxylic acid amide derivative of the formula (I) or a salt thereof can be produced by the following reactions (A) to (K), by the methods disclosed in Preparation Examples 1 to 11 given hereinafter, or by a usual process for producing a salt.

REACTION (A)

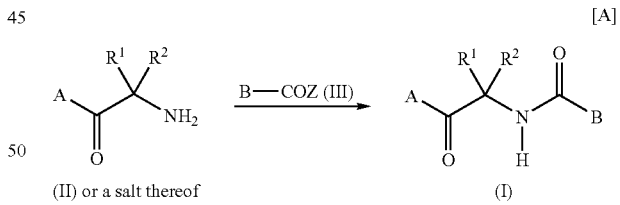

[A]

(II) or a salt thereof       (I)

In the reaction (A), A, B, $R^1$, and $R^2$, are as defined above. Z is hydroxy, alkoxy or halogen, and the halogen may be an atom of fluorine, chlorine, bromine or iodine.

Reaction (A) may be carried out usually in the presence of a base and a solvent.

The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; a pyridine such as pyridine or 4-dimethylaminopyridine; and an organic lithium such as methyllithium, n-butyl lithium or lithium diisopropyl amide. The base may be used in an amount of from 1 to 3 mols, preferably from 1 to 2 mols, per mol of the compound of the formula (II).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone, pyridine acetonitrile or propionitrile; and a ketone such as acetone or methyl ethyl ketone.

Reaction (A) may be carried out, if necessary, in the presence of a dehydration condensation agent. The dehydration condensation agent may, for example, be N,N'-dicyclohexylcarbodiimide, chlorosulfonyl isocyanate, N,N'-carbonyldiimidazole and trifluoroacetic anhydride.

The reaction temperature for reaction (A) is usually from 0 to 100° C., preferably from 0 to 50° C., and the reaction time is usually from 0.5 to 48 hours, preferably from 1 to 24 hours.

REACTION (B)

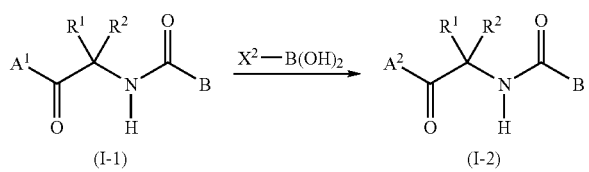

[B]

(I-1)    (I-2)

In reaction (B), B, $R^1$ and $R^2$ are as defined above, and $X^2$—$B(OH)_2$ is boronic acid (in this formula, B is boron). $A^1$ is phenyl substituted by X', benzodioxolanyl substituted by X' or benzodioxanyl substituted by X', $A^2$ is phenyl substituted by $X^2$, benzodioxolanyl substituted by $X^2$, or benzodioxanyl substituted by $X^2$, $X^1$ is an atom of chlorine, bromine or iodine, $X^2$ is phenyl which may be substituted by Y, phenoxy which may be substituted by Y, benzyloxy which may be substituted by Y, pyridyl which may be substituted by Y, or pyridyloxy which may be substituted by Y (Y is as defined above).

Reaction (B) may be carried out usually in the presence of a catalyst, a base, a solvent and an inert gas.

The catalyst may be one or more suitably selected from e.g. palladium complexes such as tetrakis (triphenylphosphine) palladium(0), bis (dibenzylideneacetone)palladium(0), and tris (dibenzylideneacetone)dipalladium(0).

The base may be one or more suitably selected from e.g. a carbonate such as sodium carbonate, potassium carbonate or calcium carbonate; a bicarbonate such as sodium bicarbonate or potassium bicarbonate; and a metal hydroxide such as sodium hydroxide or potassium hydroxide. The base may be used in an amount of from 1 to 20 mols, preferably from 1 to 10 mols, per mol of the compound of the formula (I-1).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or 1,2-dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The inert gas may, for example, be nitrogen gas or argon gas.

The reaction temperature for reaction (B) is usually from 0 to 150° C., preferably from 15 to 100° C. The reaction time is usually from 0.5 to 96 hours, preferably from 1 to 48 hours.

The compound of the formula (II) to be used in the above reaction (A) can be produced by the following reactions (C) to (E).

REACTION (C)

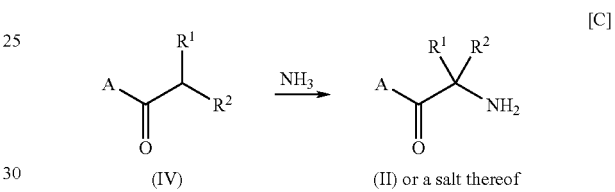

[C]

(IV)    (II) or a salt thereof

In reaction (C), A, $R^1$ and $R^2$ are as defined above. In reaction (C), a salt of the compound (II) can be produced by post treatment of the reaction or in accordance with a usual reaction for forming a salt.

Reaction (C) may be carried out usually in the presence of an oxidizing agent and a solvent.

The oxidizing agent may, for example, be potassium ferricyanide. The oxidizing agent may be used in an amount of from 1 to 10 mols, preferably from 1 to 5 mols, per mol of the compound of the formula (IV).

The solvent may be any solvent so long as it is inert to the reaction. For example, it may be one or more suitably selected from e.g. an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and water.

The reaction temperature for reaction (C) is usually from 20 to 150° C., preferably from 50 to 100° C. The reaction time is usually from 0.5 to 30 hours, preferably from 1 to 20 hours.

REACTION (D)

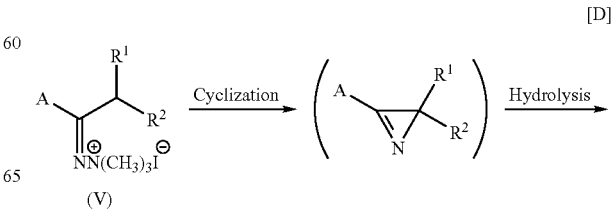

[D]

(V)

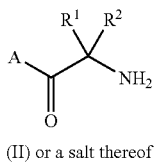

(II) or a salt thereof

In reaction (D), A, $R^1$ and $R^2$ are as defined above. In reaction (D), a salt of the compound (II) can be produced by post treatment of the reaction or in accordance with a usual reaction for forming a salt.

The cyclization reaction in reaction (D) may be carried out usually in the presence of a base and a solvent.

The base may be one or more suitably selected from e.g. an alkali metal such as sodium or potassium; an alkali metal alkoxide such as sodium methoxide, sodium ethoxide or potassium tert-butoxide; and a metal hydride such as sodium hydride or potassium hydride. The base may be used in an amount of from 1 to 3 mols, preferably from 1 to 1.5 mols per mol of the compound of the formula (V).

The solvent may be any solvent so long as it is inert to the reaction. For example, it may be one or more suitably selected from e.g. an aromatic hydrocarbon such as benzene, toluene, xylene or chlorobenzene; an ether such as dioxane, tetrahydrofuran, diethyl ether or dimethoxyethane; an alcohol such as methanol, ethanol, propanol or tert-butanol; and a nitrile such as acetonitrile, propionitrile or acrylonitrile.

The reaction temperature for the cyclization reaction in reaction (D) is usually from 0 to 150° C., preferably from 30 to 100° C. The reaction time is usually from 0.5 to 24 hours, preferably from 1 to 12 hours.

The hydrolytic reaction in reaction (D) may be carried out in accordance with a common hydrolytic reaction and may be carried out usually in the presence of an acid or base and a solvent.

The acid may, for example, be hydrogen chloride or sulfuric acid. The base may, for example, be a metal hydroxide such as sodium hydroxide or potassium hydroxide.

The solvent may be any solvent so long as it is inert to the reaction. For example, it may be one or more suitably selected e.g. an alcohol such as methanol, ethanol, propanol or tert-butanol; a nitrile such as acetonitrile, propionitrile or acrylonitrile; a ketone such as acetone or methyl ethyl ketone; and water.

The reaction temperature for the hydrolytic reaction in reaction (D) is usually from 0 to 100° C., preferably from 20 to 80° C. The reaction time is usually from 0.1 to 12 hours, preferably from 0.1 to 1 hour.

REACTION (E)

In reaction (E), A, $R^1$ and $R^2$ are as defined above. In reaction (E), a salt of the compound (II) can be produced by post treatment of the reaction or in accordance with a usual reaction for forming a salt.

The reduction reaction in reaction (E) may, for example, be catalytic reduction, reduction by a metal hydride (such as sodium boron hydride, or lithium aluminum hydride); reduction by e.g. triphenylphosphine, dimethyl sulfide or diphenyl sulfide; or reduction in a reaction system constituted by a metal such as iron or copper and a carboxylic acid such as formic acid or acetic acid. The catalytic reduction is usually carried out in a hydrogen atmosphere by using a catalyst, such as platinum, platinum oxide, platinum black, Raney Nickel, palladium, palladium-carbon, rhodium or rhodium-alumina.

Reaction (E) may be carried out usually in the presence of a solvent. The solvent may be any solvent so long as it is a solvent inert to the reaction. For example, it may be one or more suitably selected from e.g. an aromatic hydrocarbon such as benzene, toluene or xylene; an aliphatic hydrocarbon such as hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature in reaction (E) is usually from 0 to 150° C., preferably from 0 to 80° C. The reaction time is usually from 0.5 to 96 hours, preferably from 0.5 to 48 hours.

The compound of the formula (V) to be used in the above reaction (D) can be produced by the following reaction (F).

REACTION (F)

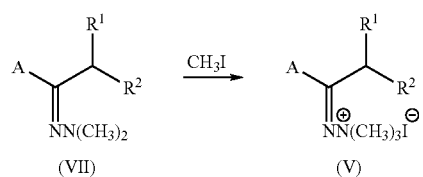

In reaction (F), A, $R^1$ and $R^2$ are as defined above.

Reaction (F) may be carried out, if necessary, in the presence of a solvent. The solvent may be any solvent so long as it is inert to the reaction, and for example, it may be one or more suitably selected from e.g. an aromatic hydrocarbon such as benzene, toluene, xylene or chlorobenzene; an aliphatic hydrocarbon such as carbon tetrachloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; an alcohol such as methanol, ethanol, propanol or tert-butanol; a nitrile such as acetonitrile, propionitrile or acrylonitrile; and a ketone such as acetone or methyl ethyl ketone.

Methyl iodide in reaction (F) may be used in an amount of from 1 to 10 mols, preferably from 1 to 3 mols, per mol of the compound of the formula (VII). Further, methyl iodide may serve also as a solvent if used excessively.

The reaction temperature for reaction (F) is usually from 0 to 100° C., preferably from 10 to 50° C. The reaction time is usually from 0.5 to 48 hours, preferably from 1 to 24 hours.

The compound of the formula (VI) to be used in the above reaction (E) can be produced by the following reaction (G).

REACTION (G)

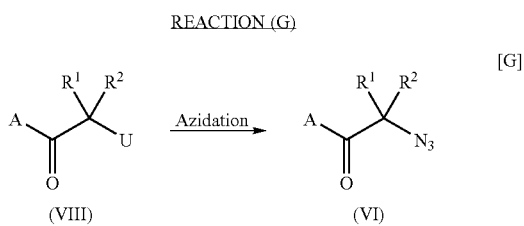

In reaction (G), A, $R^1$ and $R^2$ are as defined above, U is an atom of chlorine or bromine.

Reaction (G) may be carried out in the presence of an azidation agent. The azidation agent may be one or more suitably selected from e.g. sodium azide, potassium azide and trimethylsilyl azide.

Reaction (G) may be carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature for reaction (G) is usually from 0 to 150° C., preferably from 20 to 90° C. The reaction time is usually from 0.1 to 96 hours, preferably from 0.5 to 12 hours.

The compound of the formula (VII) to be used in the above reaction (F) can be produced by the following reaction (H).

REACTION (H)

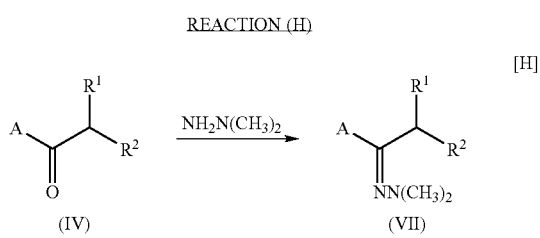

In reaction (H), A, $R^1$ and $R^2$ are as defined above.

Reaction (H) can be carried out in accordance with a common hydrazone synthetic reaction and, if necessary, in the presence of a dehydrating agent and/or a catalyst.

As the dehydrating agent, molecular sieve may, for example, be mentioned. The dehydrating agent may be used usually from 1 to 30 times, preferably from 5 to 10 times relative to the weight of the compound of the formula (IV).

The catalyst may, for example, be titanium tetrachloride.

Dimethylhydrazine for reaction (H) may be used usually in an amount of from 1 to 30 mols, preferably from 5 to 10 mols, per mol of the compound of the formula (IV).

The reaction temperature for reaction (H) is usually from 20 to 150° C., preferably from 50 to 120° C. The reaction time is usually from 5 to 200 hours, preferably from 24 to 120 hours.

The compound of the formula (VIII) to be used in the above reaction (G) can be produced by the following reaction (I).

REACTION (I)

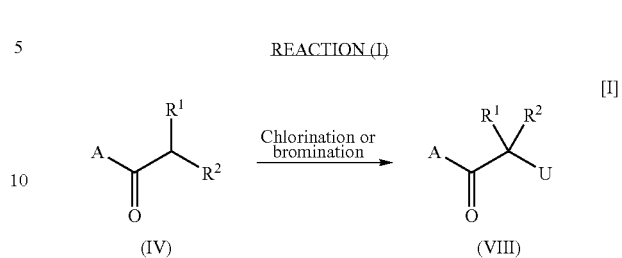

In reaction (I), A, $R^1$, $R^2$ and U are as defined above.

Reaction (I) may be carried out in the presence of a chlorination agent or a bromination agent. The chlorination agent may be one or more suitably selected from e.g. chlorine and N-chlorosuccinimide. The bromination agent may be one or more suitably selected from e.g. bromine, N-bromosuccinimide and phenyltrimethyl ammonium tribromide.

Reaction (I) may be carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; an organic acid such as acetic acid or propionic acid; and water.

Reaction (I) may be carried out, if necessary, in the presence of a base or an acid.

The base may, for example, be lithium diisopropylamide. The base is used in an amount of from 1 to 2 mols, preferably from 1 to 1.2 mols, per mol of the compound of the formula (IV).

The acid may be one or more suitably selected from e.g. an organic acid such as acetic acid or propionic acid, and Lewis acid such as aluminum chloride. The acid is usually used in a catalytic amount. Further, an organic acid as a solvent may serve as both a solvent and an acid if used excessively.

The reaction temperature for reaction (I) is usually from −100 to 150° C., preferably from −78 to 110° C. The reaction time is usually from 0.1 to 48 hours, preferably from 0.5 to 24 hours. However, if it is carried out in the presence of a base, the reaction temperature is usually from −100 to 0° C., preferably from −78 to −20° C., and the reaction time is usually from 0.1 to 12 hours, preferably from 0.5 to 6 hours. If it is carried out in the presence of an acid, the reaction temperature is usually from 0 to 150° C., preferably from 20 to 110° C., and the reaction time is usually from 0.1 to 48 hours, preferably from 1 to 24 hours.

The compound of the formula (IV) to be used in the above reaction (C), (H) or (I) is a known compound, or can be produced by the following reactions (J) or (K) or by methods in accordance therewith.

REACTION (J)

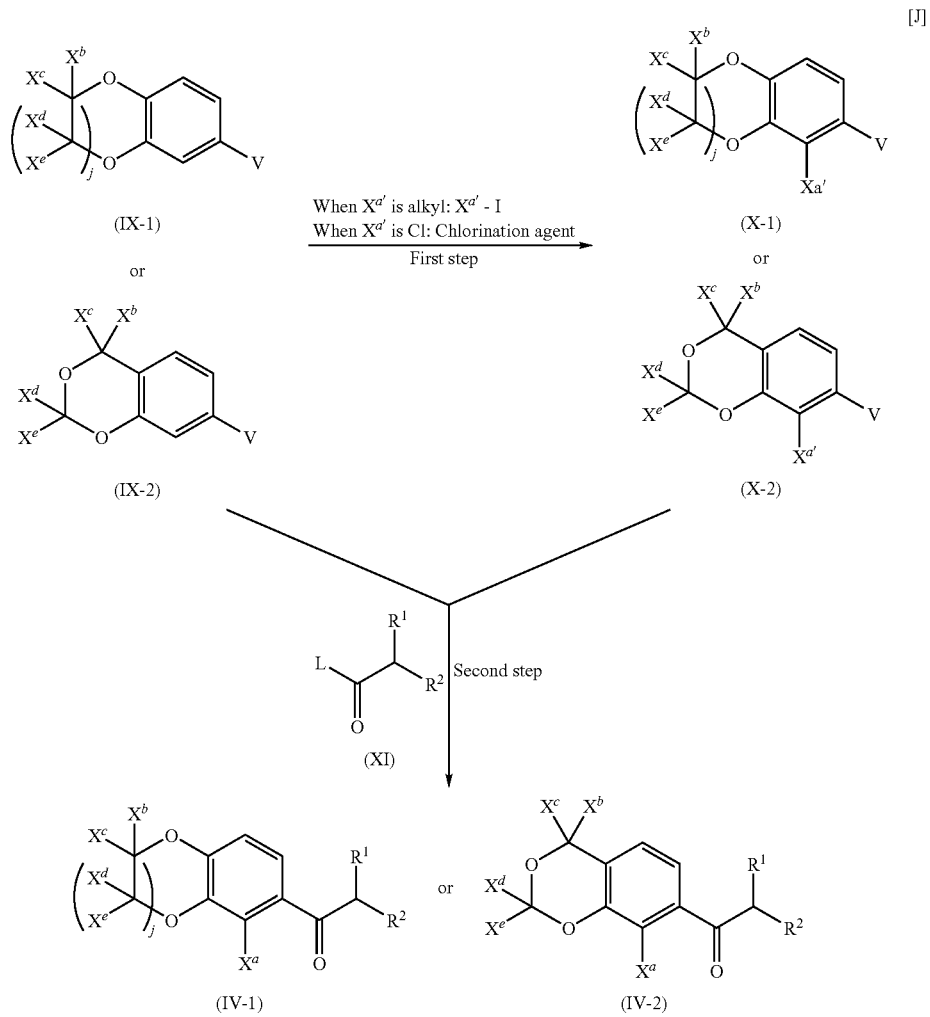

In reaction (J), $R^1$ and $R^2$ are as defined above, and $X^a$ is an hydrogen atom, chlorine atom or alkyl, is a chlorine atom or alkyl, each of $X^b$, $X^c$, $X^d$ and $X^e$ is an atom of hydrogen, fluorine or chlorine, V is an atom of bromine or iodine, j is 0 or 1, and L is a leaving group, specifically a halogen such as a chlorine atom or a bromine atom; alkoxy such as methoxy or ethoxy; dialkylamino such as dimethylamino or diethylamino; N-methoxy-N-methylamino, or aziridinyl which may be substituted by alkyl.

The first step in reaction (J) may be carried out in the presence of a base and a solvent.

The base may be suitably selected from an organic lithium compound such as lithium diisopropylamide. The base may be used in an amount of from 1 to 2 mols, preferably from 1 to 1.5 mols, per mol of the compound of the formula (IX-1) or (IX-2).

The solvent may be any solvent so long as it is a solvent inert to the reaction. For example, it may be one or more suitably selected from e.g. an ether such as dioxane, tetrahydrofuran and diethyl ether.

The chlorination agent to be used for the first step in reaction (J) may, for example, be N-chlorosuccinimide.

The formula: $X^{a'}$—I to be used for the first step in reaction (J) may be used in an amount of from 1 to 10 mols, preferably from 1 to 5 mols, per mol of the compound of the formula (IX-1) or (IX-2). Further, the chlorination agent to be used for the first step in reaction (J) is used in an amount of from 1 to 5 mols, preferably from 1 to 3 mols, per mol of the compound of the formula (IX-1) or (IX-2).

The first step in reaction (J) may be carried out, if necessary, in the presence of an inert gas. The inert gas may be suitably selected from e.g. nitrogen gas or argon gas.

The reaction temperature for the first step in reaction (J) is usually from −100 to 50° C., preferably from −70 to 25° C. The reaction time is usually from 1 to 48 hours, preferably from 1 to 20 hours.

The second step in reaction (J) may be carried out, usually in the presence of a base and a solvent.

The base may be one or more suitably selected from e.g. organic lithium compounds such as methyllithium and n-butyl lithium; and Grignard compounds such as isopropyl magnesium chloride. The base may be used in an amount of from 1 to 2 mols, preferably from 1 to 1.5 mols, per mol of the compound of the formula (IX-1), (IX-2), (X-1) or (X-2).

The solvent may be any solvent so long as it is a solvent inert to the reaction. For example, it may be one or more suitably selected from e.g. an ether such as dioxane, tetrahydrofuran and diethyl ether.

The compound of the formula (XI) to be used for the second step in reaction (J) is used in an amount of from 1 to 3 mols, preferably from 1 to 1.5 mols, per mol of the compound of the formula (IX-1), (IX-2), (X-1) or (X-2).

The second step in reaction (J) may be carried out, if necessary, in the presence of an inert gas. The inert gas may be suitably selected from e.g. nitrogen gas and argon gas.

The reaction temperature for the second step in reaction (J) is usually from −100 to 50° C., preferably from −70 to 25° C. The reaction time is usually from 1 to 48 hours, preferably from 1 to 20 hours.

The base is used in an amount of from 1 to 2 mols, preferably from 1 to 1.5 mols, per mol of the compound of the formula (IX-1), (IX-2), (X-1) or (X-2).

The solvent may be any solvent so long as it is a solvent inert to the reaction. For example, it may be one or more suitably selected from e.g. an ether such as dioxane, tetrahydrofuran and diethyl ether.

The compound of the formula (XII) to be used for the first step in reaction (K) is used in an amount of from 1 to 3 mols, preferably from 1 to 1.5 mols, per mol of the compound of the formula (IX-1), (IX-2), (X-1) or (X-2).

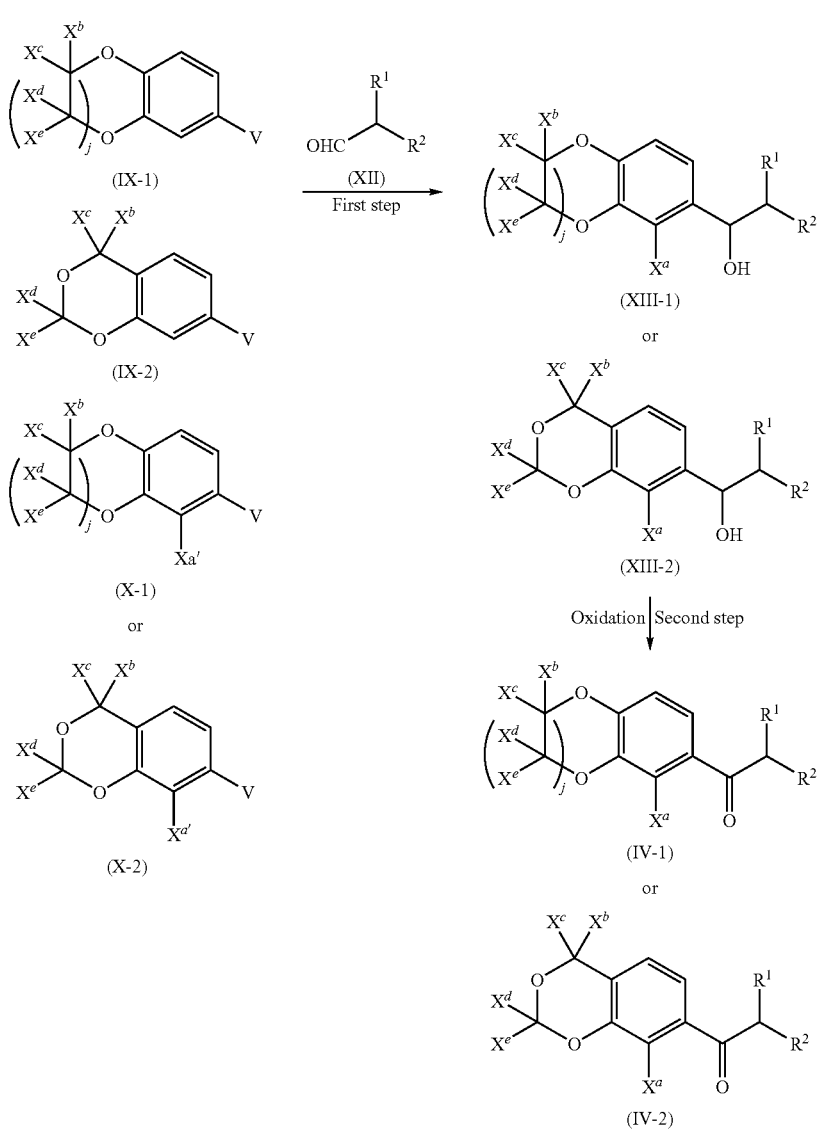

REACTION (K)

[K]

In reaction (K), $R^1$, $R^2$, $X^a$, $X^{a'}$, $X^b$, $X^c$, $X^d$, $X^e$, V and j are as defined above.

The first step in reaction (K) may be carried out usually in the presence of a base and a solvent.

The base may be one or more suitably selected from e.g. organic lithium compounds such as methyllithium and n-butyl lithium; and Grignard compounds such as isopropyl magnesium chloride.

The first step in reaction (K) may be carried out, if necessary, in the presence of an inert gas. The inert gas may be suitably selected from e.g. nitrogen gas and argon gas.

The reaction temperature for the first step in reaction (K) is usually from −100 to 50° C., preferably from −70 to 25° C. The reaction time is usually from 1 to 48 hours, preferably from 1 to 20 hours.

The second step for reaction (K) may be carried out usually in the presence of an oxidizing agent and a solvent.

The oxidizing agent may be one or more suitably selected from e.g. pyridinium chlorochromate and manganese dioxide. The oxidizing agent is used in an amount of from 1 to 10 mols, preferably from 1 to 3 mols, per mol of the compound of the formula (XIII-1) or (XIII-2).

The solvent may be any solvent so long as it is a solvent inert to the reaction. For example, it may be one or more suitably selected from e.g. an aromatic hydrocarbon such as benzene, toluene, xylene or chlorobenzene; and an aliphatic hydrocarbon such as carbon tetrachloride, methyl chloride, chloroform, dichloromethane, dichloroethane, trichloroethane, hexane or cyclohexane.

The reaction temperature for the second step in reaction (K) is usually from 0 to 150° C., preferably from 20 to 100° C. The reaction time is usually from 0.5 to 24 hours, preferably from 1 to 12 hours.

The composition of the present invention is useful as a fungicidal composition capable of controlling noxious fungi at a low dose, particularly useful as an agricultural or horticultural fungicidal composition. When used as an agricultural or horticultural fungicidal composition, the composition of the present invention is capable of controlling noxious fungi such as Oomycetes, Ascomycetes, Basidiomycetes, Deuteromycetes and particularly effective for controlling noxious fungi belonging to e.g. Ascomycetes or Deuteromycetes.

The following may be mentioned as specific examples of the above noxious fungi.

Oomycetes may, for example, be genus *Phytophthora*, such as potato or tomato late blight pathogen (*Phytophthora infestans*), or tomato haiiro-eki-byo pathogen (*Phytophthora capsici*); genus *Pseudoperonospora*, such as cucumber downy mildew pathogen (*Pseudoperonospora cubensis*); genus *Plasmopara*, such as grape downy mildew pathogen (*Plasmopara viticola*); and genus *Pythium*, such as rice seedling blight pathogen (*Pythium graminicola*), or wheat browning root rot pathogen (*Pythium iwayamai*).

Ascomycetes may, for example, be genus *Erysiphe*, such as wheat powdery mildew pathogen (*Erysiphe graminis*); genus *Sphaerotheca*, such as cucumber powdery mildew pathogen (*Sphaerotheca fuliginea*), or strawberry powdery mildew pathogen (*Sphaerotheca humuli*); genus *Uncinula*, such as grape powdery mildew pathogen (*Uncinula necator*); genus *Podosphaera*, such as apple powdery mildew pathogen (*Podosphaera leucotricha*); genus *Mycosphaerella*, such as wheat Septoria leaf blotch pathogen (*Mycosphaerella graminicola*), garden pea Mycosphaerella blight pathogen (*Mycosphaerella pinodes*), apple fruit spot pathogen (*Mycosphaerella fijiensis, Mycosphaerella pomi*), banana black sigatoka pathogen (*Mycosphaerella musicola*), persimmons circular leaf spot pathogen (*Mycosphaerella nawae*), or strawberry leaf spot pathogen (*Mycosphaerella fragariae*); genus *Venturia*, such as apple scab pathogen (*Venturia inaequalis*), or pear scab pathogen (*Venturia nashicola*); genus *Pyrenophora*, such as barley net blotch pathogen (*Pyrenophora teres*), or barley stripe pathogen (*Pyrenophora graminea*); genus *Sclerotinia*, such as various Sclerotinia disease pathogen (*Sclerotinia Sclerotiorum*) such as kidney bean stem rot pathogen, cucumber Sclerotinia rot pathogen, cabbage Sclerotinia rot pathogen, Chinese cabbage Sclerotinia rot pathogen, red pepper Sclerotinia rot pathogen, sweet pepper Sclerotinia rot pathogen, or onion watery soft rot pathogen, wheat Sclerotinia snow blight pathogen (*Sclerotinia borealis*), tomato syoryu-kinkaku pathogen (*Sclerotinia minor*), or alfalfa Sclerotinia rot and crown rot pathogen (*Sclerotinia trifoliorum*); genus *Botryolinia*, such as peanut small Sclerotinia rot pathogen (*Botryolinia arachidis*); genus *Cochliobolus*, such as rice brown spot pathogen (*Cochliobolus miyabeanus*); genus *Didymella*, such as cucumber gummy stem blight pathogen (*Didymella bryoniae*); genus *Gibberella*, such as wheat Fusarium blight pathogen (*Gibberella zeae, Gibberella avenacea*); genus *Elsinoe*, such as grape anthracnose pathogen (*Elsinoe ampelina*), or citrus scab pathogen (*Elsinoe fawcettii*); genus *Diaporthe*, such as citrus melanose pathogen (*Diaporthe citri*), or grape swelling arm pathogen (*Diaporthe sp.*); genus *Monilinia*, such as apple blossom blight pathogen (*Monilinia mali*), peach brown rot pathogen (*Monilinia fructicola*), apple or pear brown rot pathogen (*Monilinia fructigena*), or apricot brown rot pathogen (*Monilinia fructicola, Monilinia laxa*); and genus *Glomerella*, such as grape ripe rot pathogen (*Glomerella cingulata*).

Basidiomycetes may, for example, be genus *Rhizoctonia*, such as rice sheath blight pathogen (*Rhizoctonia solani*); genus *Ustilago*, such as wheat loose smut pathogen (*Ustilago nuda*); genus *Puccinia*, such as oat crown rust pathogen (*Puccinia coronata*), wheat brown rust pathogen (*Puccinia recondita*), or wheat stripe rust pathogen (*Puccinia striiformis*); genus *Typhula*, such as wheat or barley *Typhula* snow blight pathogen (*Typhula incarnata, Typhula ishikariensisis*); and genus *Phakopsora*, such as soybean rust pathogen (*Phakopsora pachyrhizi, Phakopsora meibomiae*).

Deuteromycetes may, for example, be genus *Septoria*, such as wheat glume blotch pathogen (*Septoria nodorum*), wheat speckled leaf blotch (*Septoria tritici*); genus *Botrytis*, such as various gray mold pathogen (*Botrytis cinerea*) such as grape gray mold pathogen, citrus gray mold pathogen, cucumber gray mold pathogen, tomato gray mold pathogen, strawberry gray mold pathogen, eggplant gray mold pathogen, kidney bean gray mold pathogen, adzuki bean gray mold pathogen, soybean gray mold pathogen, garden pea gray mold pathogen, peanut gray mold pathogen, red pepper gray mold pathogen, sweet pepper gray mold pathogen, lettuce gray mold pathogen, onion gray mold pathogen, statice gray mold pathogen, carnation gray mold pathogen, rose Botrytis blight pathogen, garden pansy gray mold pathogen, or sunflower gray mold pathogen, onion gray mold neck rot pathogen (*Botrytis allii*), or onion Botrytis hagare-syo (*Botrytis squamosa, Botrytis byssoidea, Botrytis tulipae*); genus *Pyricularia*, such as rice blast pathogen (*Pyricularia oryzae*); genus *Cercospora*, such as sugar beet Cercospora leaf spot pathogen (*Cercospora beticola*), or persimmons Cercospora leaf spot pathogen (*Cercospora kakivola*); genus *Colletotrichum*, such as cucumber anthracnose pathogen (*Colletotrichum orbiculare*); genus *Alternaria*, such as apple Alternaria leaf spot pathogen (*Alternaria alternata* apple pathotype), pear black spot pathogen (*Alternaria alternata* Japanese pear pathotype), potato or tomato early blight pathogen (*Alternaria solani*), cabbage or Chinese cabbage Alternaria leaf spot pathogen (*Alternaria brassicae*), cabbage Alternaria sooty spot pathogen (*Alternaria brassicola*), onion or Welsh onion Alternaria leaf spot pathogen (*Alternaria porri*); genus *Pseudocercosporella*, such as wheat eye spot pathogen (*Pseudocercosporella herpotrichoides*); genus *Pseudocercospora*, such as grape leaf spot pathogen (*Pseudocercospora vitis*); genus *Rhynchosporium*, such as barley scald pathogen (*Rhynchosporium secalis*); genus *Cladosporium*, such as peach scab pathogen (*Cladosporium carpophilum*); genus *Phomopsis*, such as peach Phomopsis rot pathogen (*Phomopsis sp.*); genus *Gloeosporium*, such as persimmons anthracnose pathogen (*Gloeosporium kaki*); genus *Fulvia*, such as tomato leaf mold pathogen (*Fulvia fulva*); genus *Corynespora*, such as cucumber Corynespora leaf spot pathogen (*Corynespora cassiicola*); and genus *Cylindrosporum*; such as tomato kappan-byo pathogen (*Cylindrosporum* sp.).

The composition of the present invention is capable of controlling the above various noxious fungi and thus capable of preventively or curatively controlling various diseases. Particularly, the composition of the present invention is effective for controlling various diseases which are problematic in the agricultural and horticultural field, such as blast, brown spot, sheath blight or damping-off of rice (*Oryza sativa*, etc.); powdery mildew, scab, brown rust, stripe rust, net blotch, stripe, snow mold, snow blight, loose smut, eye spot, scald, leaf spot or glume blotch of cereals (*Hordeum vulgare, Tricum aestivum*, etc.); melanose or scab of citrus (*Citrus* spp., etc.); blossom blight, powdery mildew, melanose, Alternaria leaf spot or scab of apple (*Malus pumila*); scab or black spot of pear (*Pyrus serotina, Pyrus ussuriensis, Pyrus communis*); brown rot, scab or Phomopsis rot of peach (*Prunus persica*, etc.); anthracnose, ripe rot, leaf spot, swelling arm, powdery mildew or downy mildew of grape (*Vitis vinifera* spp., etc.); anthracnose, circular leaf spot or Cercospora leaf spot of Japanese persimmon (*Diospyros kaki*, etc.); anthracnose, powdery mildew, gummy stem blight, corynespora leaf spot or downy mildew of cucurbit (*Cucumis melo*, etc.); early blight, haiiro-eki-byo, leaf, mold or late blight of tomato (*Lycopersicon esculentum*); black sigatoka of banana (*Musa sapientum*, etc.); Cercospora leaf spot of sugar beet (*Beta vulgaris* var. *saccharifera*, etc.); Mycosphaerella blight of garden pea (*Pisum sativum*); various Alternaria disease pathogens of cruciferous vegetables (*Brassica* sp., *Raphanus* sp., etc); late blight or early blight of potato (*Solanum tuberosum*); powdery mildew or leaf spot of strawberry (*Fragaria*, etc.); and gray mold or disease caused by *Sclerotinia* of various crops such as beans, vegetables, fruits or flowers. Among them, the composition of the present invention is particularly effective for controlling plant diseases caused by Ascomycetes or Deuteromycetes, i.e. various plant diseases such as gray mold, diseases caused by *Sclerotinia*, powdery mildew, blast, glume blotch, or plant diseases caused by *Alternaria*.

Specifically, the composition of the present invention is particularly effective against various gray mold of cucumber (*Cucumis sativus*), kidney bean (*Phaseolus vulgaris*), adzuki bean (*Vigna angularis*), soybean (*Glycine max*), garden pea, peanut (*Arachis hypogaea*), tomato, strawberry, eggplant (*Solanum melongena*), red pepper (*Capsicum annuum*), sweet pepper (*Capsicum annuum*), lettuce (*Lactuca sativa*), onion (*Allium cepa*), grape, citrus, statice (*Limonium* spp.), carnation (*Dianthus* spp.), rose (*Rosa* spp.), garden pansy (*Viola*, etc.) or sunflower (*Helianthus annuus*); diseases caused by *Sclerotinia*, of kidney bean (*Phaseolus vulgaris*), cucumber (*Cucumis sativus*), cabbage (*Brassica oleracea* var. *capitata*), chinese cabbage (*Brassica rapa*), red pepper (*Capsicum annuum*), sweet pepper (*Capsicum annuum*) or onion (*Allium cepa*); powdery mildew of wheat (*Triticum aestivum*), cucumber (*Cucumis sativus*), strawberry, grape or apple (*Malus pumila* var. *domestica*); wheat glume blotch; apple Alternaria blotch; pears black spot; potato early blight, and cabbage or chinese cabbage Alternaria leaf spot.

Further, the composition of the present invention is effective also for preventive or curative control of soil diseases caused by plant pathogens such as *Fusarium, Pythium, Rhizoctonia, Verticillium* and *Plasmodiophora*.

Still further, the composition of the present invention is effective also to control various pathogens resistant to fungicides such as benzimidazoles, diethofencarb, strobilurins, dicarboximides, phenylamides, fluazinam, quinoxyfen, cyflufenamide, ergosterol biosynthesis inhibitors and melanin biosynthesis inhibitors.

Furthermore, the composition of the present invention has an excellent penetrative, systemic property, and when a pesticide containing the composition of the present invention is applied to soil, it is possible to control noxious fungi on stems and leaves at the same time as controlling noxious fungi in soil.

The composition of the present invention, is usually formulated by mixing the carboxylic acid amide derivative represented by the formula (I) or a salt thereof with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, N,N-dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyethylene glycol, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Each of the components as such adjuvants may be one or more suitable selected for use, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the carboxylic acid amide derivative represented by the formula (I) or a salt thereof to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various spreaders e.g. surfactants, vegetable oils or mineral oils may be added thereto, as the case requires.

The application of the composition of the present invention can not generally be defined, as it varies depending upon the weather conditions, the type of the formulation, the crop plants to be treated, the application season, the application site, the types or germination states of noxious fungi, and the types or degree of outbreak of the diseases. However, it is usually applied in a concentration of the active ingredient being from 0.1 to 10,000 ppm, preferably from 1 to 2,000 ppm in the case of foliage treatment, and its dose may be such that the carboxylic acid amide derivative of the formula (I) or a salt thereof is usually from 0.1 to 50,000 g, preferably from 1 to 30,000 g, per hectare. In the case of soil treatment, it is applied usually in such a dose that the carboxylic acid amide derivative of the formula (I) or a salt thereof is from 10 to 100,000 g, preferably from 200 to 20,000 g, per hectare.

The formulation containing the composition of the present invention or a diluted product thereof may be applied by an application method which is commonly used, such as spreading (spreading, spraying, misting, atomizing, grain diffusing or application on water surface), soil application (such as mixing or irrigation) or surface application (such as coating, dust coating or covering). Further, it may be applied also by so-called ultra low volume. In this method, the formulation may contain 100% of the active ingredient.

The composition of the present invention may be mixed with or may be used in combination with other agricultural chemicals, fertilizers or phytotoxicity-reducing agents, whereby synergistic effects or activities may sometimes be obtained. Such other agricultural chemicals may, for example, be a herbicide, an insecticide, a miticide, a nematicide, a soil pesticide, a fungicide, an antivirus agent, an attractant, an antibiotic, a plant hormone and a plant growth regulating agent. Especially, with a mixed fungicidal composition having the carboxylic acid amide derivative of the formula (I) or a salt thereof mixed with or used in combination with one or more of other fungicidally active ingredient compounds, the application range, the application time, the fungicidal activities, etc. may be improved to preferred directions. Here, the carboxylic acid amide derivative of the formula (I) or a salt thereof, and the active ingredient compound of another fungicide may separately be formulated so that they may be mixed for use at the time of application, or they may be formulated together for use. The present invention includes such a mixed fungicidal composition.

The mixing ratio of the carboxylic acid amide derivative of the formula (I) or a salt thereof to another fungicidally active ingredient compound can not generally be defined, since it varies depending upon the weather conditions, the types of formulations, the crops to be treated, the application time, the application site, the types or germination state of noxious fungi, the types or state of the diseases, etc., but it is usually within a range of from 1:300 to 300:1, preferably from 1:100 to 100:1, by weight. Further, the dose for the application may be such that the total amount of the active compounds is from 0.1 to 70,000 g, preferably from 1 to 30,000 g, per hectare. The present invention includes a method for controlling noxious fungi by an application of such a mixed fungicidal composition.

The active ingredient compound (common name; including some which are under application or test code of the Japan plant protection association) of the fungicide in such another agricultural chemical, may, for example, be:

an anilinopyrimidine compound such as Mepanipyrim, Pyrimethanil or Cyprodinil;

a pyridinamine compound such as Fluazinam;

an azole compound such as Triadimefon, Bitertanol, Triflumizole, Etaconazole, Propiconazole, Penconazole, Flusilazole, Myclobutanil, Cyproconazole, Tebuconazole, Hexaconazole, Furconazole-cis, Prochloraz, Metconazole, Epoxiconazole, Tetraconazole, Oxpoconazole fumarate, Sipconazole, Prothioconazole, Triadimenol, Flutriafol, Difenoconazole, Fluquinconazole, Fenbuconazole, Bromuconazole, Diniconazole, Tricyclazole, Probenazole, Simeconazole, Pefurazoate, Ipconazole or Imibenconazole;

a quinoxaline compound such as Quinomethionate;

a dithiocarbamate compound such as Maneb, Zineb, Mancozeb, Polycarbamate, Metiram, Propineb or Thiram;

an organic chlorine compound such as Fthalide, Chlorothalonil or Quintozene;

an imidazole compound such as Benomyl, Thiophanate-Methyl, Carbendazim, Thiabendazole, Fuberiazole or Cyazofamid;

a cyano acetamide compound such as Cymoxanil;

a phenylamide compound such as Metalaxyl, Metalaxyl-M, Oxadixyl, Mefenoxam, Ofurace, Benalaxyl, Benalaxyl-M (another name; Kiralaxyl or Chiralaxyl), Furalaxyl or Cyprofuram;

a sulfenic acid compound such as Dichlofluanid;

a copper compound such as Cupric hydroxide or Oxine Copper;

an isoxazole compound such as Hymexazol;

an organic phosphorus compound such as Fosetyl-Al, Tolcofos-Methyl, S-benzyl O,O-diisopropylphosphorothioate, O-ethyl S,S-diphenylphosphorodithioate or aluminum ethylhydrogen phosphonate;

an N-halogenothioalkyl compound such a Captan, Captafol or Folpet;

a dicarboxylmide compound such as Procymidone, Iprodione or Vinclozolin;

a benzanilide compound such as Flutolanil, Mepronil, Zoxamid or Tiadinil;

an anilide compound such as Carboxin, Oxycarboxin, Thifluzamide, MTF-753 (Penthiopyrad) or Boscalid;

a piperazine compound such as Triforine;

a pyridine compound such as Pyrifenox;

a carbinol compound such as Fenarimol or Flutriafol;

a piperidine compound such as Fenpropidine;

a morpholine compound such as Fenpropimorph or Tridemorph;

an organic tin compound such as Fentin Hydroxide or Fentin Acetate;

an urea compound such as Pencycuron;

a cinnamic acid compound such as Dimethomorph or Flumorph;

a phenylcarbamate compound such as Diethofencarb;

a cyanopyrrole compound such as Fludioxonil or Fenpiclonil;

a strobilurin compound such as Azoxystrobin, Kresoxim-Methyl, Metominofen, Trifloxystrobin, Picoxystrobin, Oryzastrobin, Dimoxystrobin, Pyraclostrobin, Fluoxastrobin or Fluacrypyrin;

an oxazolidinone compound such as Famoxadone;

a thiazolecarboxamide compound such as Ethaboxam;

a silylamide compound such as Silthiopham;

an amino acid amide carbamate compound such as Iprovalicarb or Benthiavalicarb-isopropyl;

an imidazolidine compound such as Fenamidone;

a hydroxyanilide compound such as Fenhexamid;
a benzenesulfonamide compound such as Flusulfamide;
an oxime ether compound such as Cyflufenamid;
a phenoxyamide compound such as Fenoxanil;
an antibiotic such as Validamycin, Kasugamycin or Polyoxins;
a guanidine compound such as Iminoctadine;
other compound, such as Isoprothiolane, Pyroquilon, Diclomezine, Quinoxyfen, Propamocarb Hydrochloride, Spiroxamine, Chloropicrin, Dazomet, Metam-sodium, Metrafenone, UBF-307, Diclocymet, Proquinazid, Amisulbrom (another name: Amibromdol), KIF-7767 (KUF-1204, Pyribencarb methyl, Mepyricarb), Syngenta 446510 (Mandipropamid, Dipromandamid) or Fluopicolide.

The active ingredient compound (common name; including some which are under application) of the insecticide, miticide, nematicide or soil pesticide in such another agricultural chemical, may, for example, be:

an organic phosphate compound such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos, Disulfoton, Chlorpyrifos, Demeton-S-methyl; Dimethoate, Methamidophos or Imicyafos;

a carbamate compound such as Carbaryl, Propoxur, Aldicarb, Carbofuran, Thiodicarb, Methomyl, Oxamyl, Ethiofencarb, Pirimicarb, Fenobucarb, Carbosulfan or Benfuracarb;

a nelicetoxin derivative such as Cartap, Thiocyclam or Bensultap;

an organic chlorine compound such as Dicofol, Tetradifon or Endosulfan;

an organic metal compound such as Fenbutatin Oxide;

a pyrethroid compound such as Fenvalerate, Permethrin, Cypermethrin, Deltamethrin, Cyhalothrin, Tefluthrin, Ethofenprox, Fenpropathrin or Bifenthrin;

a benzoyl urea compound such as Diflubenzuron, Chlorfluazuron; Teflubenzuron, Flufenoxuron, Lufenuron or Novaluron;

a juvenile hormone-like compound such as Methoprene, Pyriproxyfen or Fenoxycarb;

a pyridadinone compound such as Pyridaben;

a pyrazole compound such as Fenpyroximate, Fipronil, Tebufenpyrad, Ethiprole, Tolfenpyrad, Acetoprole, Pyrafluprole or Pyriprole;

a neonicotinoide such as Imidacloprid, Nitenpyram, Acetamiprid, Thiacloprid, Thiamethoxam, Clothianidin or Dinotefuran;

a hydrazine compound such as Tebufenozide, Methoxyfenozide, Chromafenozide or Halofenozide;

a dinitro compound, an organosulfur compound, an urea compound, a triazine compound or a hydrazone compound;

other compound, such as Flonicamid, Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazine, 1,3-dichloropropene, Diafenthiuron, Benclothiaz, Flufenerim, Pyridalyl, Spirodiclofen, Bifenazate, Spiromesifen, spirotetramat, Propargite, Clofentezine, Fluacrypyrim, Metaflumizone, Flubendiamide, Cyflumetofen, Chlorantraniliprole, Cyenopyrafen, Pyrifluquinazon or Fenazaquin.

Further; a microbial pesticide such as a BT agent, an insect pathogenic virus agent, entomopathogenic fugi or nematophagous fugi;

an antibiotic such as Avermectin, Emamectin-Benzoate, Milbemectin, Spinosad, Ivermectin or Lepimectin;

a natural product such as Azadirachtin or Rotenone.

Preferred embodiments of the present invention are as follows. However, it should be understood that the present invention is by no means restricted to such is specific embodiments.

(1) A fungicidal composition containing a carboxylic acid amide derivative of the formula (I) or a salt thereof as an active ingredient, wherein B is 2-pyridyl which may be substituted.

(2) A fungicidal composition containing a carboxylic acid amide derivative of the formula (I) or a salt thereof as an active ingredient, wherein A is phenyl which may be substituted by X, benzodioxolanyl which may be substituted by X, or benzodioxanyl which may be substituted by X; B is 2-pyridyl which may be substituted; each of $R^1$ and $R^2$ is alkyl, or $R^1$ and $R^2$ may together form a 3- to 6-membered saturated carbon ring; X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, phenyl substituted by Y, phenoxy substituted by Y, pyridyl substituted by Y, or pyridyloxy substituted by Y; and Y is halogen, alkyl, haloalkyl, alkenyl, haloalkenyl, alkynyl, haloalkynyl or alkoxy.

(3) A fungicidal composition containing a carboxylic acid amide derivative of the formula (I) or a salt thereof as an active ingredient, wherein A is phenyl substituted by halogen, alkyl or alkoxy; B is 2-pyridyl substituted by halogen, alkyl or haloalkyl; each of $R^1$ and $R^2$ is alkyl.

(4) The fungicidal composition according to the above (3), wherein A is phenyl substituted by at least two substituents selected from the group consisting of halogen, alkyl and alkoxy.

(5) A fungicidal composition containing a carboxylic acid amide derivative of the formula (I) or a salt thereof as an active ingredient, wherein B is 3-pyridyl which may be substituted.

(6) A fungicidal composition containing a carboxylic acid amide derivative of the formula (I) or a salt thereof as an active ingredient, wherein A is phenyl which may be substituted by X, benzodioxolanyl which may be substituted by X, or benzodioxanyl which may be substituted by X; B is 3-pyridyl which may be substituted; each of $R^1$ and $R^2$ is alkyl, or $R^1$ and $R^2$ may together form a 3- to 6-membered saturated carbon ring; X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, phenyl substituted by Y, phenoxy substituted by Y, pyridyl substituted by Y, or pyridyloxy substituted by Y; and Y is halogen, alkyl, haloalkyl, alkenyl, haloalkenyl, alkynyl, haloalkynyl or alkoxy.

(7) A fungicidal composition containing a carboxylic acid amide derivative of the formula (I) or a salt thereof as an active ingredient, wherein A is phenyl substituted by halogen, alkyl or alkoxy; B is 3-pyridyl substituted by halogen, alkyl or haloalkyl; each of $R^1$ and $R^2$ is alkyl.

(8) The fungicidal composition according to the above (7), wherein A is phenyl substituted by at least two substituents selected from the group consisting of halogen, alkyl and alkoxy.

(9) A fungicidal composition containing a carboxylic acid amide derivative of the formula (I) or a salt thereof as an active ingredient, wherein A is benzodioxolanyl substituted by halogen or alkyl; B is 2- or 3-pyridyl substituted by halogen, alkyl or haloalkyl; each of $R^1$ and $R^2$ is alkyl.

(10) A fungicidal composition containing a carboxylic acid amide derivative of the formula (I) or a salt thereof as an active ingredient, wherein A is benzodioxanyl substituted by halogen or alkyl; B is 2- or 3-pyridyl substituted by halogen, alkyl or haloalkyl; each of $R^1$ and $R^2$ is alkyl.

(11) A fungicidal composition containing a carboxylic acid amide derivative of the formula (I) or a salt thereof as an active ingredient, wherein A is 2-alkyl-3-halogen-substituted phenyl; B is 2-pyridyl substituted by haloalkyl; and each of $R^1$ and $R^2$ is alkyl.

(12) A fungicidal composition containing a carboxylic acid amide derivative of the formula (I) or a salt thereof as an active ingredient, wherein A is 2-alkyl-4-halogen-substituted phenyl; B is 2-pyridyl substituted by haloalkyl; and each of $R^1$ and $R^2$ is alkyl.

(13) A fungicidal composition containing a carboxylic acid amide derivative of the formula (I) or a salt thereof as an active ingredient, wherein A is 2-alkyl-4-alkoxy-substituted phenyl; B is 2-pyridyl substituted by haloalkyl; and each of $R^1$ and $R^2$ is alkyl.

(14) A fungicidal composition containing a carboxylic acid amide derivative of the formula (I) or a salt thereof as an active ingredient, wherein A is 4-alkoxy-substituted phenyl; B is 2-pyridyl substituted by haloalkyl; and each of $R^1$ and $R^2$ is alkyl.

(15) A carboxylic acid amide derivative of the above formula (I) or a salt thereof.

(16) A carboxylic acid amide derivative of the above formula (I) or a salt thereof, wherein B is 2-pyridyl which may be substituted.

(17) A carboxylic acid amide derivative of the above formula (I-a) or a salt thereof.

(18) A carboxylic acid amide derivative of the above formula (I-a) or a salt thereof, wherein $A^a$ is phenyl substituted by halogen, alkyl or alkoxy; $B^a$ is 2-pyridyl substituted by halogen, alkyl or haloalkyl; and each of $R^1$ and $R^2$ is alkyl.

(19) The carboxylic acid amide derivative or a salt thereof according to the above (18), wherein $A^a$ is phenyl substituted by at least two substituents selected from the group consisting of halogen, alkyl and alkoxy.

(20) A carboxylic acid amide derivative of the above formula (I-a) or a salt thereof, wherein $A^a$ is 2-alkyl-3-halogen-substituted phenyl; $B^a$ is 2-pyridyl substituted by haloalkyl; and each of $R^1$ and $R^2$ is alkyl.

(21) A carboxylic acid amide derivative of the above formula (I-a) or a salt thereof, wherein $A^a$ is 2-alkyl-4-halogen-substituted phenyl; $B^a$ is 2-pyridyl substituted by haloalkyl; and each of $R^1$ and $R^2$ is alkyl.

(22) A carboxylic acid amide derivative of the above formula (I-a) or a salt thereof, wherein $A^a$ is 2-alkyl-4-alkoxy-substituted phenyl; $B^a$ is 2-pyridyl substituted by haloalkyl; and each of $R^1$ and $R^2$ is alkyl.

(23) A carboxylic acid amide derivative of the above formula (I-a) or a salt thereof, wherein $A^a$ is 4-alkoxy-substituted phenyl; $B^a$ is 2-pyridyl substituted by haloalkyl; and each of $R^1$ and $R^2$ is alkyl.

(24) A carboxylic acid amide derivative of the above formula (I) or a salt thereof, wherein B is 3-pyridyl which may be substituted.

(25) A carboxylic acid amide derivative of the above formula (I) or a salt thereof, wherein A is phenyl substituted by halogen, alkyl or alkoxy; B is 3-pyridyl substituted by halogen, alkyl or haloalkyl; and each of $R^1$ and $R^2$ is alkyl.

(26) The carboxylic acid amide derivative or a salt thereof according to the above (25), wherein A is phenyl substituted by at least two substituents selected from the group consisting of halogen, alkyl and alkoxy.

(27) A carboxylic acid amide derivative of the above formula (I) or a salt thereof, wherein A is benzodioxolanyl substituted by halogen or alkyl; B is 2- or 3-pyridyl substituted by halogen, alkyl or haloalkyl; and each of $R^1$ and $R^2$ is alkyl.

(28) A carboxylic acid amide derivative of the above formula (I) or a salt thereof, wherein A is benzodioxanyl substituted by halogen or alkyl; B is 2- or 3-pyridyl substituted by halogen, alkyl or haloalkyl; and each of $R^1$ and $R^2$ is alkyl.

(29) A mixed fungicidal composition comprising a carboxylic acid amide derivative of the above formula (I) or a salt thereof, and another fungicially active ingredient compound, as active ingredients.

(30) The mixed fungicidal composition according to the above (29), wherein said another fungicidally active ingredient compound is at least one member selected from the group consisting of an anilinopyrimidine compound, a pyridinamine compound, an azole compound, a quinoxaline compound, a dithiocarbamate compound, an organic chlorine compound, an imidazole compound, a cyano acetamide compound, a phenylamide compound, a sulfenic acid compound, a copper compound, an isoxazole compound, an organic phosphorus compound, an N-halogenothioalkyl compound, a dicarboxylmide compound, a benzanilide compound, an anilide compound, a piperazine compound, a pyridine compound, a carbinol compound, a piperidine compound, a morpholine compound, an organic tin compound, an urea compound, a cinnamic acid compound, a phenylcarbamate compound, a cyanopyrrole compound, a strobilurin compound, an oxazolidinone compound, a thiazolecarboxamide compound, a silylamide compound, an amino acid amide carbamate compound, an imidazolidine compound, a hydroxyanilide compound, a benzenesulfonamide compound, an oxime ether compound, a phenoxyamide compound, an antibiotic, a guanidine compound, Isoprothiolane, Pyroquilon, Diclomezine, Quinoxyfen, Propamocarb hydrochloride, Spiroxamine, Chloropicrin, Dazomet, Metam-sodium, Metrafenone, UBF-307, Diclocymet, Proquinazid, Amisulbrom, KIF-7767, Syngenta 446510 and Fluopicolide.

(31) The mixed fungicidal composition according to the above (29), wherein said another fungicidally active ingredient compound is at least one member selected from the group consisting of an anilinopyrimidine compound, a pyridinamine compound, an azole compound, a dithiocarbamate compound, an organic chlorine compound, an imidazole compound, a copper compound, a dicarboxylmide compound, an anilide compound, a piperazine compound, a pyridine compound, a carbinol compound, a phenylcarbamate compound, a cyanopyrrole compound, a strobilurin compound, a hydroxyanilide compound and KIF-7767.

(32) The mixed fungicidal composition according to the above (29), wherein said another fungicidally active ingredient compound is at least one member selected from the group consisting of Mepanipyrim, Pyrimethanil, Cyprodinil, Fluazinam, Triadimefon, Bitertanol, Triflumizole, Etaconazole, Propiconazole, Penconazole, Flusilazole, Myclobutanil, Cyproconazole, Tebuconazole, Hexaconazole, Furconazole-cis, Prochloraz, Metconazole, Epoxiconazole, Tetraconazole, Oxpoconazole fumarate, Sipconazole, Prothioconazole, Triadimenol, Flutriafol, Difenoconazole, Fluquinconazole, Fenbuconazole, Bromuconazole, Diniconazole, Tricyclazole, Probenazole, Simeconazole, Pefurazoate, Ipconazole, Imibenconazole, Maneb, Zineb, Mancozeb, Polycarbamate, Metiram, Propineb, Fthalide, Chlorothalonil, Quintozene, Benomyl, Thiophanate-Methyl, Carbendazim, Cyazofamid, Cupric hydroxide, Oxine Copper, Procymidone, Iprodione, Vinclozolin, Boscalid, Diethofencarb, Fludioxonil, Fenpiclonil, Azoxystrobin, Kresoxim-Methyl, Metominofen, Trifloxystrobin, Picoxystrobin, Oryzastrobin, Dimoxystrobin, Pyraclostrobin, Fluoxastrobin, Fluacrypyrin, Fenhexamid, Polyoxins, Iminoctadine, MTF-753 and KIF-7767.

(33) A method for controlling noxious fungi, which comprises applying an effective amount of a carboxylic acid amide derivative of the above formula (I) or a salt thereof.

(34) A method for controlling noxious fungi, which comprises applying an effective amount of a carboxylic acid amide derivative of the above formula (I-a) or a salt thereof.

(35) The method for controlling noxious fungi according to the above (33) or (34), wherein the noxious fungi are Ascomycetes or Deuteromycetes.

(36) A method for controlling plant diseases, which comprises applying an effective amount of a carboxylic acid amide derivative of the above formula (I) or a salt thereof.

(37) A method for controlling plant diseases, which comprises applying an effective amount of a carboxylic acid amide derivative of the above formula (I-a) or a salt thereof.

(38) The method for controlling plant diseases according to the above (36) or (37), wherein the plant diseases are plant diseases caused by Ascomycetes or Deuteromycetes.

(39) The method for controlling plant diseases according to the above (38), wherein the plant diseases caused by Ascomycetes or Deuteromycetes are gray mold, diseases caused by *Sclerotinia*, powdery mildew, blast, glume blotch or plant diseases caused by *Alternaria*.

(40) A method for protecting crop plants, which comprises applying an effective amount of a carboxylic acid amide derivative of the above formula (I) or a salt thereof.

(41) A method for protecting crop plants, which comprises applying an effective amount of a carboxylic acid amide derivative of the above formula (I-a) or a salt thereof.

(42) A method for improving crop yields, which comprises applying an effective amount of a carboxylic acid amide derivative of the above formula (I) or a salt thereof.

(43) A method for improving crop yields, which comprises applying an effective amount of a carboxylic acid amide derivative of the above formula (I-a) or a salt thereof.

Now, the present invention will be described in further detail with reference to Examples. However, it should be understood that the present invention is by no means restricted to thereto. Firstly, Preparations for the carboxylic acid amide derivative of the formula (I) or a salt thereof will be described.

Preparation Example 1

Preparation of N-[(3'-difluoromethoxy-1,1-dimethyl) phenacyl]-3-trifluoromethyl-2-pyridinecarboxamide (after-mentioned compound No. 1-21)

(1) A Grignard reagent prepared by using 0.75 g of magnesium, 4.46 g of 2-bromopropane and 24 ml of anhydrous diethyl ether, was dropwise added to a mixture comprising 4.09 g of 3-difluoromethoxybenzonitrile and 20 ml of anhydrous diethyl ether. After completion of the dropwise addition, the mixture was reacted at room temperature for 27 hours. The reaction mixture was put into ice water, and 6N sulfuric acid was added to bring the mixture to be weakly, acidic, followed by stirring for 0.5 hour. The mixture was extracted with diethyl ether and washed with water. The organic layer was dried over anhydrous magnesium sulfate and then concentrated under reduced pressure. The residue was purified by silica gel column chromatography (developing solvent: ethyl acetate/n-hexane=1/19), to obtain 2.04 g of 3-difluoromethoxyisobutyrophenone. The NMR spectrum data of this product is as follows.
$^1$H-NMR δppm (Solvent: CDCl$_3$/300 MHz)
1.23 (d, 6H), 3.52 (m, 1H), 6.56 (t, 1H), 7.32 (dd, 1H), 7.48 (t, 1H), 7.70 (s, 1H), 7.80 (d, 1H)

(2) 3.58 g of phenyltrimethylammonium tribromide was added to a mixture comprising 2.04 g of 3-difluoromethoxyisobutyrophenone and 30 ml of tetrahydrofuran, followed by a reaction for 2 hours at room temperature. The reaction mixture was filtered, and the filtrate was concentrated under reduced pressure to obtain 2.79 g of oily α-bromo-3-difluoromethoxyisobutyrophenone.

(3) 1.24 g of sodium azide was added to a mixture comprising 2.79 g of α-bromo-3-difluoromethoxyisobutyrophenone and 35 ml of dimethyl sulfoxide, followed by a reaction for 1 hour at 50° C. The reaction mixture was put into water and extracted with ethyl acetate, followed by washing with water. The organic layer was dried over anhydrous magnesium sulfate and then concentrated under reduced pressure. The residue was purified with silica gel column chromatography (developing solvent: ethyl acetate/n-hexane=1/9) to obtain 2.21 g of oily α-azide-3-difluoromethoxyisobutyrophenone. The NMR spectrum data of this product is as follows.
$^1$H-NMR δppm (Solvent: CDCl$_3$/300 MHz)
1.61 (s, 6H), 6.56 (t, 1H), 7.34 (dd, 1H), 7.48 (t, 1H), 7.86 (s, 1H), 7.98 (d, 1H)

(4) A mixture comprising 2.18 g of α-azide-3-difluoromethoxyisobutyrophenone, 35 ml of methanol and 0.109 g of 5% palladium carbon, was reacted for 1.5 hours at room temperature in a hydrogen atmosphere. The reaction mixture was filtered through celite, and the filtrate was concentrated under reduced pressure. To the residue, ethyl acetate was added, and hydrogen chloride gas was introduced under cooling with ice, followed by concentration under reduced pressure to obtain 1.76 g of α-amino-3-difluoromethoxyisobutyrophenone hydrochloride.

(5) 0.33 g of triethylamine was added to a mixture comprising 0.3 g of α-amino-3-difluoromethoxyisobutyrophenone hydrochloride and 10 ml of 1,2-dichloroethane, and a mixture comprising 0.26 g of 3-trifluoromethylpicolinic acid chloride and 5 ml of 1,2-dichloroethane, was dropwise added under cooling with ice. After completion of the dropwise addition, the mixture was reacted at room temperature for 2 hours. The reaction mixture was washed with water, and the organic layer was dried over anhydrous sodium sulfate and then concentrated under reduced pressure. The residue was purified by silica gel column chromatography (developing solvent: ethyl acetate/n-hexane=2/3) to obtain 0.35 g of the desired product having a melting point of from 81 to 83° C. The NMR spectrum data of this product is as follows.
$^1$H-NMR δppm (Solvent: CDCl$_3$/400 MHz) 1.80 (s, 6H), 6.48 (t, 1H), 7.21 (dd, 1H), 7.36 (t, 1H), 7.57 (dd, 1H), 7.78 (s, 1H), 7.87 (d, 1H), 8.10 (d, 1H), 8.18 (s, 1H), 8.75 (d, 1 H)

Preparation Example 2

Preparation of N-[(3',4'-dichloro-1,1-dimethyl) phenacyl]-3-trifluoromethyl-2-pyridinecarboxamide (after-mentioned compound No. 1-9)

(1) A mixture comprising 10.0 g of 3,4-dichlorobenzoyl chloride, 9.31 g of ethyl 2-bromoisobutyrate and 90 ml of anhydrous diethyl ether, was dropwise added to 3.12 g of zinc in a nitrogen atmosphere, followed by a reaction for 15 hours under reflux. The reaction mixture was filtered through celite, and the filtrate was washed with 20% sulfuric acid and then with water. The organic layer was dried over anhydrous magnesium sulfate and then concentrated under reduced pressure. The residue was purified by silica gel column chromatography (developing solvent: ethyl acetate/n-hexane=1/19) to obtain 8.7 g of oily ethyl 2-(3', 4'-dichlorobenzoyl)isobutyrate. The NMR spectrum data of this product is as follows.

$^1$H-NMR δppm (Solvent: CDCl$_3$/400 MHz)

1.11 (t, 3H), 1.52 (s, 6H), 4.14 (q, 2H), 7.48 (d, 1H), 7.63 (dd, 1H), 7.96 (d, 1H)

(2) A mixture comprising 8.7 g of ethyl 2-(3',4'-dichlorobenzoyl)isobutyrate, 14.2 ml of sulfuric acid, 14.2 ml of water and 40 ml of acetic acid, was reacted for 15 hours under reflux. The reaction mixture was put into ice water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/19) to obtain 6.47 g of oily 3,4-dichloroisobutyrophenone. The NMR spectrum data of this product is as follows.

$^1$H-NMR δppm (Solvent: CDCl$_3$/400 MHz)

1.21 (d, 6H), 3.46 (m, 1H), 7.55 (d, 1H), 7.79 (dd, 1H), 8.02 (d, 1H)

(3) 9.32 g of phenyltrimethylammonium tribromide was added to a mixture comprising 6.47 g of 3,4-dichloroisobutyrophenone and 100 ml of tetrahydrofuran, followed by a reaction for 4 hours at room temperature. The reaction mixture was filtered, and the filtrate was concentrated under reduced pressure to obtain 6.39 g of oily α-bromo-3,4-dichloroisobutyrophenone. The NMR spectrum data of this product is as follows.

$^1$H-NMR δppm (Solvent: CDCl$_3$/300 MHz)

2.01 (s, 6H), 7.50 (d, 1H), 8.0 (dd, 1H), 8.20 (d, 1H)

(4) 2.8 g of sodium azide was added to a mixture comprising 6.39 g of α-bromo-3,4-dichloroisobutyrophenone and 60 ml of dimethylsulfoxide, followed by a reaction for 1 hour at 50° C. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/9) to obtain 6.34 g of oily α-azide-3,4-dichloroisobutyrophenone. The NMR spectrum data of this product is as follows.

$^1$H-NMR δppm (Solvent: CDCl$_3$/300 MHz)

1.60 (s, 6H), 7.53 (d, 1H), 7.97 (dd, 1H), 8.20 (d, 1H)

(5) 7.74 g of triphenylphosphine was added to a mixture comprising 6.34 g of α-azide-3,4-dichloroisobutyrophenone, 90 ml of tetrahydrofuran and 3.2 ml of water, followed by a reaction for 23 hours at room temperature. The reaction mixture was concentrated under reduced pressure, and to the residue, water and then hydrochloric acid were added to make it weakly acidic, followed by washing with diethyl ether. The aqueous layer was neutralized with an aqueous sodium hydroxide solution and extracted with diethyl ether. The organic layer was dried over anhydrous magnesium sulfate and then concentrated under reduced pressure. Ethyl acetate was added to the residue, and hydrogen chloride gas was introduced under cooling with ice. The formed solid was collected by filtration and dried to obtain 5.92 g of α-amino-3,4-dichloroisobutyrophenone hydrochloride.

(6) 0.33 g of triethylamine was added to a mixture comprising 0.3 g of α-amino-3,4-dichloroisobutyrophenone hydrochloride and 10 ml of 1,2-dichloroethane, followed by stirring for 0.2 hour at room temperature. The mixture was then cooled with ice, and a mixture comprising 0.27 g of 3-trifluoromethylpicolinic acid chloride and 2 ml of 1,2-dichloroethane, was dropwise added, followed by a reaction for 1.5 hours at room temperature. The reaction mixture was diluted with dichloromethane and washed with water. The organic layer was dried over anhydrous sodium sulfate and then concentrated under reduced pressure. The residue was purified by silica gel column chromatography (developing solvent: ethyl acetate/n-hexane=2/3) to obtain 0.29 g of the desired product having a melting point of from 106 to 109° C. The NMR spectrum data of this product is as follows.

$^1$H-NMR δppm (Solvent: CDCl$_3$/400 MHz)

1.77 (s, 6H), 7.41 (d, 1H), 7.57 (dd, 1H), 7.87 (dd, 1H), 8.10-8.12 (m, 2H), 8.14 (d, 1H), 8.76 (d, 1H)

Preparation Example 3

Preparation of N-[(4'-methoxy-2'-methyl-1,1-dimethyl)phenacyl]-3-trifluoromethyl-2-pyridinecarboxamide (after-mentioned compound No. 1-3)

(1) A mixture comprising 5.7 g of isobutyryl chloride and 5 ml of carbon disulfide, was dropwise added to a mixture comprising 7.15 g of aluminum chloride and 20 ml of carbon disulfide at a temperature of not higher than 10° C., followed by a reaction for 0.5 hour. Then, a mixture comprising 5.0 g of m-cresol and 5 ml of carbon disulfide, was dropwise added at a temperature of not higher than 5° C., followed by a reaction for 4 hours at room temperature. The reaction mixture was put into a mixture of ice water and hydrochloric acid and extracted with methylene chloride, followed by washing with water. The organic layer was dried over anhydrous sodium sulfate and then concentrated under reduced pressure. To the residue, 60 ml of tetrahydrofuran, 30 ml of water and 3.7 g of sodium hydroxide were added, followed by a reaction for 1.5 hours at room temperature. The reaction mixture was concentrated under reduced pressure, then put into ice water, weakly acidified with dilute sulfuric acid and extracted with ethyl acetate. The organic layer was dried over anhydrous magnesium sulfate and then concentrated under reduced pressure. The residue was purified by silica gel column chromatography (developing solvent: ethyl acetate/n-hexane=1/9) to obtain 2.45 g of solid 4-hydroxy-2-methylisobutyrophenone. The NMR spectrum data of this product is as follows.

$^1$H-NMR δppm (Solvent: CDCl$_3$/400 MHz)

1.15 (d, 6H), 2.43 (s, 3H), 3.40 (m, 1H), 6.70 (m, 2H), 7.57 (d, 1 H)

(2) A mixture comprising 0.62 g of dimethyl sulfate and 3 ml of dimethylformamide, was added to a mixture comprising 0.8 g of 4-hydroxy-2-methylisobutyrophenone, 0.68 g of potassium carbonate and 15 ml of dimethylformamide, followed by a reaction for 3 hours at room temperature. The reaction mixture was put into water, extracted with ethyl acetate and washed with water. The organic layer was dried over anhydrous magnesium sulfate and then concentrated under reduced pressure. The residue was purified by silica gel column chromatography (developing solvent: ethyl acetate/n-hexane=1/9) to obtain 0.59 g of oily 4-methoxy-2-methylisobutyrophenone. The NMR spectrum data of this product is as follows.

$^1$H-NMR δppm (Solvent: CDCl$_3$/400 MHz)

1.13 (d, 6H), 2.46 (s, 1H), 3.38 (m, 1H), 6.72 (m, 2H), 7.59 (d, 1 H)

(3) 1.16 g of phenyltrimethylammonium tribromide was added to a mixture comprising 0.59 g of 4-methoxy-2-methylisobutyrophenone and 15 ml of tetrahydrofuran, followed by a reaction for 2.5 hours at room temperature. Diethyl ether was added to the reaction mixture, and an insoluble matter was filtered off. The filtrate was concentrated under reduced pressure to obtain 0.7 g of oily α-bromo-4-methoxy-2-methylisobutyrophenone. 0.4 g of sodium azide was added to a mixture comprising 0.7 g of α-bromo-4-methoxy-2-methylisobutyrophenone and 8 ml of dimethylsulfoxide, followed by a reaction for 1.5 hours at 50° C. The reaction mixture was put into water, extracted with ethyl acetate and then washed with water. The organic layer was dried over anhydrous magnesium sulfate and then concentrated under reduced pressure. The residue was purified by silica gel column chromatography (developing solvent: ethyl acetate/n-hexane=1/9) to obtain 0.67 g of oily α-azide-4-methoxy-2-methylisobutyrophenone. The NMR spectrum data of this product is as follows.
$^1$H-NMR δppm (Solvent: CDCl$_3$/300 MHz)
1.54 (s, 6H), 2.33 (s, 1H), 3.81 (s, 3H), 6.72 (dd, 1H), 6.75 (d, 1H), 7.61 (d, 1H)

(4) A mixture comprising 0.19 g of α-azide-4-methoxy-2-methylisobutyrophenone, 10 ml of methanol and 13 mg of 5% palladium carbon, was reacted for 1 hour at room temperature in a hydrogen atmosphere. The reaction mixture was filtered through celite, and the filtrate was concentrated under reduced pressure to obtain 0.17 g of oily α-amino-4-methoxy-2-methylisobutyrophenone.

(5) 0.10 g of triethylamine was added to a mixture comprising 0.17 g of α-amino-4-methoxy-2-methylisobutyrophenone and 10 ml of tetrahydrofuran, and a mixture comprising 0.1.7 g of 3-trifluoromethylpicolinic acid chloride and 2 ml of tetrahydrofuran, was dropwise added thereto under cooling with ice. After completion of the dropwise addition, the mixture was reacted for 1 hour at room temperature. The reaction mixture was extracted with ethyl acetate and washed with water. The organic layer was dried over anhydrous magnesium sulfate and then concentrated under reduced pressure. The residue was purified by silica gel column chromatography (developing solvent: ethyl acetate/n-hexane=3/7) to obtain 0.25 g of the desired product having a melting point of from 116 to 118° C. The NMR spectrum data of this product is as follows.
$^1$H-NMR δppm (Solvent: CDCl$_3$/300 MHz)
1.81 (s, 6H), 2.38 (s, 3H), 3.79 (s, 3H), 6.65 (dd, 1H), 6.76 (d, 1H), 7.49 (d, 1H), 7.53 (dd, 1H), 8.11 (d, 1H), 8.40 (s, 1H), 8.73 (d, 1H)

Preparation Example 4

Preparation of N-[2-[(2,2-difluoro-4-methyl-1,3-benzodioxolan-5-yl)carbonyl]-2-propyl]-3-trifluoromethyl-2-pyridinecarboxamide (after-mentioned compound No. 2-1)

(1) 52.7 ml of n-butyl lithium (1.56 M n-hexane solution) was dropwise added to a mixture comprising 8.77 g of diisopropylamine and 150 ml of tetrahydrofuran in a nitrogen atmosphere at −20° C., followed by stirring for 30 minutes at the same temperature. At a temperature of not higher than −50° C., 15.0 g of 5-bromo-2,2-difluoro-1,3-benzodioxolane was dropwise added, followed by stirring for 30 minutes at the same temperature. 19.7 ml of methyl iodide was dropwise added at a temperature of not higher than −70° C., then the mixture was heated to room temperature and reacted for 15 hours. After completion of the reaction, the reaction mixture was put into water, weakly acidified with hydrochloric acid, and then extracted with diethyl ether. The organic layer was washed with water, dried over magnesium sulfate and concentrated under reduced pressure. The residue was purified by silica gel column chromatography (developing solvent: n-hexane) to obtain 12.54 g of oily 5-bromo-2,2-difluoro-4-methyl-1,3-benzodioxolane. The NMR spectrum data of this product is as follows.
$^1$H-NMR ppm (Solvent: CDCl$_3$/400 MHz)
2.34 (s, 3H), 6.79 (d, 1H), 7.27 (d, 1H)

(2) 35.2 ml of n-butyl lithium (1.56 M n-hexane solution) was dropwise added to a mixture comprising 12.54 g of 5-bromo-2,2-difluoro-4-methyl-1,3-benzodioxolane and 150 ml of diethyl ether at −50° C. in a nitrogen atmosphere, followed, by stirring for 30 minutes at the same temperature. At a temperature of not higher than −70° C., 5.4 g of isobutylaldehyde was dropwise added, and then, the mixture was heated to room temperature and reacted for 15 hours. After completion of the reaction; the reaction mixture was put into water, weakly acidified with hydrochloric acid and extracted with diethyl ether. The organic layer was washed with water, dried over magnesium sulfate and concentrated under reduced pressure. The residue was purified by silica gel column chromatography (developing solvent: ethyl acetate/n-hexane=1/9) to obtain 10.65 g of oily 1-(2,2-difluoro-4-methyl-1,3-benzodioxolan-5-yl)-2-methylpropanol. The NMR spectrum data of this product is as follows.
$^1$H-NMR δppm (Solvent: CDCl$_3$/400 MHz)
0.84 (d, 3H), 1.02 (d, 3H), 1.94 (m, 1H), 2.29 (s, 3H), 4.57 (m, 1H), 6.90 (d, 1H), 7.14 (d, 1H)

(3) A mixture comprising 10.65 g of 1-(2,2-difluoro-4-methyl-1,3-benzodioxolan-5-yl)-2-methylpropanol and 35 ml of dichloromethane, was added to a mixture comprising 11.7 g of pyridinium chlorochromate, 5.94 g of sodium acetate and 100 ml of dichloromethane at room temperature, followed by a reaction for 2 hours at the same temperature with stirring. After completion of the reaction, the reaction mixture was filtered through celite, and the filtrate was concentrated under reduced pressure. The residue was purified by silica gel column chromatography (developing solvent: ethyl acetate/n-hexane=1/19) to obtain 8.64 g of oily 5-(2,2-difluoro-4-methyl-1,3-benzodioxolanyl)2-propyl ketone. The NMR spectrum data of this product is as follows.
$^1$H-NMR δppm (Solvent: CDCl$_3$/400 MHz)
1.16 (d, 6H), 2.40 (s, 3H), 3.35 (m, 1H), 6.94 (d, 1H), 7.39 (d, 1 H)

(4) 13.41 g of phenyltrimethylammonium tribromide was added to a mixture comprising 8.64 g of 5-(2,2-difluoro-4-methyl-1,3-benzodioxolanyl)2-propyl ketone and 86 ml of tetrahydrofuran, followed by a reaction for 2 hours at room temperature. After completion of the reaction, the reaction mixture was filtered, and the filtrate was concentrated under reduced pressure to obtain 11.4 g of oily 2-bromo-2-propyl 5-(2,2-difluoro-4-methyl-1,3-benzodioxolanyl)ketone. 4.64 g of sodium azide was added to a mixture comprising 11.4 g of 2-bromo-2-propyl 5-(2,2-difluoro-4-methyl-1,3-benzodioxolanyl)ketone and 69.6 ml of dimethylsulfoxide, followed by a reaction for 2 hours at 50° C. After completion of the reaction, the reaction mixture was put into water, extracted with diethyl ether and then washed with water. The organic layer was dried over anhydrous magnesium sulfate, and then concentrated under reduced pressure. The residue was purified by silica gel column chromatography (developing solvent: ethyl acetate/n-hexane=1/19) to obtain 9.6 g of oily 2-azide-2-propyl 5-(2,2-difluoro-4-methyl-1,3-benzodioxolanyl)ketone. The NMR spectrum data of this product is as follows.
$^1$H-NMR δppm (solvent: CDCl$_3$/400 MHz)
1.57 (s, 6H), 2.27 (s, 3H), 6.94 (d, 1H), 7.38 (d, 1H)

(5) A mixture comprising 0.20 g of 2-azide-2-propyl 5-(2,2-difluoro-4-methyl-1,3-benzodioxolanyl)ketone, 5 ml of methanol and 20 mg of 5% palladium carbon, was reacted for 1 hour at room temperature in a hydrogen atmosphere. After completion of the reaction, the reaction mixture was filtered through celite, and the filtrate was concentrated under reduced pressure to obtain 0.18 g of oily 2-amino-2-propyl 5-(2,2-difluoro-4-methyl-1,3-benzodioxolanyl)ketone. 86 mg of triethylamine was added to a mixture comprising 0.18 g of 2-amino-2-propyl 5-(2,2-difluoro-4-methyl-1,3-benzodioxolanyl)ketone and 7 ml of 1,2-dichloroethane, and 0.15 g of 3-trifluoromethylpicolinic acid chloride was dropwise added thereto under cooling with ice. After completion of the dropwise addition, the mixture was reacted for 1.5 hours at room temperature. After completion of the reaction, the reaction mixture was washed with water, dried over anhydrous sodium sulfate, and then concentrated under reduced pressure. The residue was purified by silica gel column chromatography (developing solvent: ethyl acetate/h-hexane=3/7) to obtain 0.20 g of the desired product having a melting point of from 130 to 134° C. The NMR spectrum data of this product is as follows.
$^1$H-NMR δppm (Solvent: CDCl$_3$/400 MHz)
1.79 (s, 6H), 2.37 (s, 3H), 6.77 (d, 1H), 7.31 (d, 1H), 7.55 (dd, 1H), 8.11 (d, 1H), 8.16 (s, 1H), 8.72 (d, 1H)

Preparation Example 5

Preparation of N-[[3'-(2-propyloxy)-1,1-dimethyl]phenacyl]-3-trifluoromethyl-2-pyridinecarboxamide (after-mentioned compound No. 1-131)

Using 5.0 g of 3-isopropyloxybenzonitrile, 0.97 g of a viscous desired product was obtained in the same, manner as in the above Preparation Example 1(1) to (5). The NMR spectrum data of this product is as follows.
$^1$H-NMR δppm (Solvent: CDCl$_3$/400 MHz)
1.28 (d, 6H), 1.82 (s, 6H), 4.55 (m, 1H), 6.97 (dd, 1H), 7.21 (d, 1H), 7.47 (d, 1H), 7.53 (m, 2H), 8.10 (d, 1H), 8.73 (d, 1H)

Preparation Example 6

Preparation of N[(3'-hydroxy-1,1-dimethyl)phenacyl]-3-trifluoromethyl-2-pyridinecarboxamide (after-mentioned compound No. 1-130)

0.51 g of titanium tetrachloride was added to a mixture comprising 0.70 g of N-[[3'-(2-propyloxy)-1,1-dimethyl]phenacyl]-3-trifluoromethyl-2-pyridinecarboxamide and 20 ml of methylene chloride under cooling with ice. Then, 0.36 g of aluminum chloride was added, and then, the mixture was returned to room temperature and reacted for 13 hours. The reaction mixture was put into ice and extracted with methylene chloride. The organic layer was dried over anhydrous sodium sulfate and then concentrated under reduced pressure to obtain 0.61 g of a viscous desired product. The NMR spectrum data of this product is as follows.
$^1$H-NMR δppm (Solvent: CDCl$_3$/400 MHz)
1.78 (s, 6H), 6.93 (dd, 1H), 7.18 (t, 1H), 7.51 (d, 1H), 7.55 (m, 2H), 8.11 (d, 1H), 8.32 (s, 1H), 8.72 (d, 1H)

Preparation Example 7

Preparation of N-[[3'-(2-pentyloxy)-1,1-dimethyl]phenacyl]-3-trifluoromethyl-2-pyridinecarboxamide (after-mentioned compound No. 1-136)

0.18 g of potassium carbonate, 2 mg of tetra n-butylammonium bromide and 0.23 g of 2-bromopentane were added to a mixture comprising 0.25 g of N-[(3'-hydroxy-1,1-dimethyl)phenacyl]-3-trifluoromethyl-2-pyridinecarboxamide and 10 ml of dimethylformamide, followed by a reaction for 27 hours at 50° C. The reaction mixture was put into water, extracted with diethyl ether and washed with water. The organic layer was dried over anhydrous sodium sulfate and then, concentrated under reduced pressure. The residue was purified by silica gel column chromatography (developing solvent: ethyl acetate/n-hexane=2/3) to obtain 0.25 g of a viscous desired product. The NMR spectrum data of this product is as follows.
$^1$H-NMR δppm (Solvent: CDCl$_3$/400 MHz)
0.88 (t, 3H), 1.22 (d, 3H), 1.38 (s, 6H), 4.36 (m, 1H), 6.96 (dd, 1H), 7.21 (t, 1H), 7.47 (d, 1H), 7.52 (m, 2H), 8.09 (d, 1H), 8.36 (s, 1H), 8.72 (d, 1H)

Preparation Example 8

Preparation of N-[[4'-(2-propyloxy)-1,1-dimethyl]phenacyl]-3-trifluoromethyl-2-pyridinecarboxamide (after-mentioned compound No. 1-42)

Using 10.0 g of 4-isopropyloxybenzonitrile, 2.8 g of the desired product having a melting point of from 118 to 120° C. was obtained in the same manner as in the above Preparation Example 1(1) to (5). The NMR spectrum data of this product is as follows.
$^1$H-NMR δppm (Solvent: CDCl$_3$/400 MHz)
1.31 (d, 6H), 1.85 (s, 6H), 4.59 (m, 1H), 6.82 (d, 2H), 7.53 (dd, 1H), 8.03 (d, 2H), 8.09 (d, 1H), 8.48 (s, 1H), 8.74 (d, 1H)

Preparation Example 9

Preparation of N-[(4'-hydroxy-1,1-dimethyl)phenacyl]-3-trifluoromethyl-2-pyridinecarboxamide (after-mentioned compound No. 1-71)

2.02 g of titanium tetrachloride was added to a mixture comprising 2.8 g of N-[[4'-(2-propyloxy)-1,1-dimethyl]phenacyl]-3-trifluoromethyl-2-pyridinecarboxamide and 70 ml of methylene chloride under cooling with ice. Then, 1.42 g of aluminum chloride was added, and then, the mixture was returned to room temperature and reacted for 16 hours. The reaction mixture was put into ice, and methylene chloride was added; followed by stirring. An insoluble matter was filtered off, and a solid was dissolved in ethyl acetate and washed with water. The obtained product was dried over anhydrous sodium sulfate and then concentrated under reduced pressure to obtain 2.3 g of the desired product having a melting point of from 238 to 240° C. The NMR spectrum data of this product is as follows.
$^1$H-NMR δppm (Solvent: CDCl$_3$/400 MHz)
1.59 (s, 6H), 6.59 (d, 2H), 7.38 (dd, 1H), 7.80 (d, 2H), 7.91 (d, 1H), 8.37 (s, 1H), 8.58 (d, 1H)

Preparation Example 10

Preparation of N-[(4'-cyclopentyloxy-1,1-dimethyl)phenacyl]-3-trifluoromethyl-2-pyridinecarboxamide (after-mentioned compound No. 1-72)

0.12 g of potassium carbonate and 0.34 g of cyclopentyl iodide were added to a mixture comprising 0.15 g of N-[(4'-hydroxy-1,1-dimethyl)phenacyl]-3-trifluoromethyl-2-pyridinecarboxamide and 8 ml of dimethylformamide, followed by a reaction for 20 hours at 90° C. The reaction mixture was put into water, extracted with diethyl ether and washed with water. The organic layer was washed with an aqueous sodium hydroxide solution and washed with water. Then, it was dried over anhydrous sodium sulfate and concentrated under reduced pressure. To the residue, n-hexane was added, and the solid was collected by filtration to obtain 0.14 g of the desired product having a melting point of from 132 to 134° C. The NMR spectrum data of this product is as follows.

$^1$H-NMR δppm (Solvent: CDCl$_3$/400 MHz)
1.58 (m, 4H), 1.70-1.90 (m, 4H), 1.84 (s, 6H), 4.78 (m, 1H), 6.81 (d, 2H), 7.53 (dd, 1H), 8.03 (d, 2H), 8.09 (d, 1H), 8.49 (s, 1H), 8.74 (d, 1H)

Preparation Example 11

Preparation of N-[[4'-(2-heptyloxy)-1,1-dimethyl]phenacyl]-3-trifluoromethyl-2-pyridinecarboxamide (after-mentioned compound No. 1-119)

(1) Using 25.0 g of 4-isopropyloxybenzonitrile, 22.4 g of oily α-azide-4-isopropyloxyisobutyrophenone was obtained in the same manner as in the above Preparation Example 1 (1) to (3). The NMR spectrum data of this product is as follows.

$^1$H-NMR δppm (Solvent: CDCl$_3$/400 MHz)
1.34 (d, 6H), 1.64 (s, 6H), 4.63 (m, 1H), 6.88 (d, 2H), 8.13 (d, 2 H)

(2) 1.1 g of titanium tetrachloride was added to a mixture comprising 1.38 g of α-azide-4-isopropyloxyisobutyrophenone and 20 ml of methylene chloride under cooling with ice. Then, 0.75 g of aluminum chloride was added, and the mixture was returned to room temperature and reacted for 17 hours. The reaction mixture was put into ice and extracted with ethyl acetate. The organic layer was dried over anhydrous sodium sulfate and then concentrated under reduced pressure to obtain 1.1 g of oily α-azide-4-hydroxyisobutyrophenone. The NMR spectrum data of this product is as follows.

$^1$H-NMR δppm (Solvent: CDCl$_3$/400 MHz)
1.58 (s, 6H), 6.86 (d, 2H), 8.11 (d, 2H)

(3) A mixture comprising 1.02 g of diethylazodicarboxylate (40% toluene solution) and 2 ml of tetrahydrofuran, was dropwise added to a mixture comprising 0.40 g of α-azide-4-hydroxyisobutyrophenone, 0.25 g of 2-heptanol, 0.61 g of triphenylphosphine and 10 ml of tetrahydrofuran, followed by a reaction for 1 hour at room temperature. The reaction mixture was concentrated under reduced pressure, and the residue was purified by silica gel column chromatography (developing solvent: ethyl acetate/n-hexane=5/95) to obtain 0.34 g of oily α-azide-4-(2-heptyloxy)isobutyrophenone. The NMR spectrum data of this product is as follows.

$^1$H-NMR δppm (Solvent: CDCl$_3$/400 MHz)
0.82 (t, 3H), 1.22-1.37 (m, 7H), 1.26 (d, 3H), 1.53 (s, 6H), 1.68 (m, 1H), 4.39 (m, 1H), 6.82 (d, 2H), 8.08 (d, 2H)

(4) A mixture comprising 0.34 g of α-azide-4-(2-heptyloxy)isobutyrophenone, 15 ml of methanol and 20 mg of 5% palladium carbon, was reacted for 3.5 hours at room temperature in a hydrogen atmosphere. The reaction mixture was filtered through celite, and the filtrate was concentrated under reduced pressure to obtain 0.25 g of oily α-amino-4-(2-heptyloxy)isobutyrophenone.

(5) 55 mg of triethylamine was added to a mixture comprising 0.125 g of α-amino-4-(2-heptyloxy)isobutyrophenone and 10 ml of tetrahydrofuran, and a mixture comprising 0.10 g of 3-trifluoromethylpicolinic acid chloride and 2 ml of tetrahydrofuran, was dropwise added under cooling with ice. After completion of the dropwise addition, the mixture was reacted for 2 hours at room temperature. After adding water, the reaction mixture was extracted with ethyl acetate and washed with water. The organic layer was dried over anhydrous sodium sulfate and then concentrated under reduced pressure. The residue was purified by silica gel column chromatography (developing solvent: ethyl acetate/n-hexane=1/2) to obtain 0.13 g of the desired product having a melting point of from 99 to 101° C. The NMR spectrum data of this product is as follows.

$^1$H-NMR δppm (Solvent: CDCl$_3$/400 MHz)
0.80 (t, 3H), 1.22 (t, 3H), 1.22-1.35 (m, 5H), 1.49 (m, 1H), 1.66 (m, 1H), 4.35 (m, 1H), 6.76 (d, 2H), 7.47 (dd, 1H), 7.98 (d, 2H), 8.04 (d, 1H), 8.43 (s, 1H), 8.69 (d, 1H)

Now, typical examples of the carboxylic acid amide derivative of the formula (I) or a salt thereof are specifically disclosed in Tables 1 and 2. These compounds can be prepared on the basis of the above-mentioned Preparation Examples or the above-mentioned various production processes. In the Tables, No. represents compound No. Further, Me represents methyl, Et ethyl, Pr(n) normal propyl, Pr(i) isopropyl, Bu(n) normal butyl, Bu(i) isobutyl, Bu(sec) secondary butyl, and Ph phenyl. Further, with respect to those having the physical properties not shown by the melting points, the NMR spectrum data are shown in Table 3.

TABLE 1

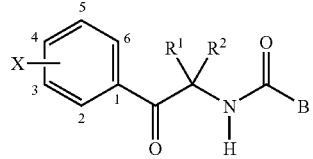

| No. | R$^1$ | R$^2$ | X | B | Physical property (melting point ° C.) |
|---|---|---|---|---|---|
| 1-1 | Me | Me | 2-Me-4-Cl | 3-CF$_3$-2-pyridyl | 125-130 |
| 1-2 | Me | Me | 2-Me-4-Br | 3-CF$_3$-2-pyridyl | 115-118 |
| 1-3 | Me | Me | 2-Me-4-OMe | 3-CF$_3$-2-pyridyl | 116-118 |
| 1-4 | Me | Me | 2-Me-4-OBu(sec) | 3-CF$_3$-2-pyridyl | 82-84 |

TABLE 1-continued

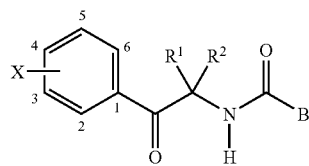

| No. | R¹ | R² | X | B | Physical property (melting point °C.) |
|---|---|---|---|---|---|
| 1-5 | Me | Me | 3-Me-4-Cl | 3-$CF_3$-2-pyridyl | 104-107 |
| 1-6 | Me | Me | 3-Me-4-Br | 3-$CF_3$-2-pyridyl | 103-106 |
| 1-7 | Me | Me | 4-Br | 3-$CF_3$-2-pyridyl | 115-120 |
| 1-8 | Me | Me | 2-Me-4-OEt | 3-$CF_3$-2-pyridyl | 70-75 |
| 1-9 | Me | Me | 3-Cl-4-Cl | 3-$CF_3$-2-pyridyl | 106-109 |
| 1-10 | Me | Me | 2-Me-4-OPr(i) | 3-$CF_3$-2-pyridyl | 98-100 |
| 1-11 | Me | Me | 2-Me-4-OPr(n) | 3-$CF_3$-2-pyridyl | 88-90 |
| 1-12 | Me | Me | 2-Me-4-OBu(n) | 3-$CF_3$-2-pyridyl | 54-57 |
| 1-13 | Me | Me | 2-Me-3-Cl | 3-$CF_3$-2-pyridyl | viscous |
| 1-14 | Me | Me | 2-Me-4-OEt | 3-Cl-2-pyridyl | 70-75 |
| 1-15 | Me | Me | 2-Me-4-OPr(i) | 3-Cl-2-pyridyl | 72-76 |
| 1-16 | Me | Me | 2-Me-4-OPr(i) | 3-Me-2-pyridyl | 82-85 |
| 1-17 | Me | Me | 3-Cl-4-Cl | 3-Me-2-pyridyl | 102-106 |
| 1-18 | Me | Me | 2-Me-4-OPr(i) | 2-Br-3-pyridyl | 119-121 |
| 1-19 | Me | Me | 2-Me-4-OPr(i) | 2-Me-3-pyridyl | 148-158 |
| 1-20 | Me | Me | 2-Me-4-OPr(i) | 2-$CF_3$-3-pyridyl | 97-100 |
| 1-21 | Me | Me | 3-$OCHF_2$ | 3-$CF_3$-2-pyridyl | 81-83 |
| 1-22 | Me | Me | 2-Me-4-OPr(i) | 3-Br-2-pyridyl | 74-78 |
| 1-23 | Me | Me | 2-Me-4-OPr(i) | 2-Cl-3-pyridyl | 120-124 |
| 1-24 | Me | Me | 2-Me-4-OPr(i) | 4-$CF_3$-3-pyridyl | 122-128 |
| 1-25 | Me | Me | 3-Cl-4-Cl | 2-Cl-3-pyridyl | 136-140 |
| 1-26 | Me | Me | 3-Cl | 3-$CF_3$-2-pyridyl | 105-108 |
| 1-27 | Me | Me | 3-Br | 3-$CF_3$-2-pyridyl | 117-118 |
| 1-28 | Me | Me | 2-Me-3-OPr(n) | 3-$CF_3$-2-pyridyl | 107-109 |
| 1-29 | Me | Me | 3-OPr(n) | 3-$CF_3$-2-pyridyl | 103-106 |
| 1-30 | Me | Me | 3-OBu(n) | 3-$CF_3$-2-pyridyl | |
| 1-31 | Me | Me | 3-$(CH_2)_4CH_3$ | 3-$CF_3$-2-pyridyl | |
| 1-32 | Me | Me | 3-$O(CH_2)_4CH_3$ | 3-$CF_3$-2-pyridyl | |
| 1-33 | Me | Me | 3-$(CH_2)_5CH_3$ | 3-$CF_3$-2-pyridyl | |
| 1-34 | Me | Me | 3-$O(CH_2)_5CH_3$ | 3-$CF_3$-2-pyridyl | 59-65 |
| 1-35 | Me | Me | 3-$(CH_2)_6CH_3$ | 3-$CF_3$-2-pyridyl | |
| 1-36 | Me | Me | 3-SBu(n) | 3-$CF_3$-2-pyridyl | |
| 1-37 | Me | Me | 3-$S(CH_2)_4CH_3$ | 3-$CF_3$-2-pyridyl | |
| 1-38 | Me | Me | 3-$S(CH_2)_5CH_3$ | 3-$CF_3$-2-pyridyl | |
| 1-39 | Me | Me | 4-OMe | 3-$CF_3$-2-pyridyl | |
| 1-40 | Me | Me | 4-OEt | 3-$CF_3$-2-pyridyl | 114-118 |
| 1-41 | Me | Me | 4-OPr(n) | 3-$CF_3$-2-pyridyl | |
| 1-42 | Me | Me | 4-OPr(i) | 3-$CF_3$-2-pyridyl | 118-120 |
| 1-43 | Me | Me | 4-OBu(sec) | 3-$CF_3$-2-pyridyl | 105-108 |
| 1-44 | Me | Me | 3-OMe | 3-$CF_3$-2-pyridyl | |
| 1-45 | Me | Me | 3-OEt | 3-$CF_3$-2-pyridyl | |
| 1-46 | Me | Me | 4-OBu(n) | 3-$CF_3$-2-pyridyl | 103-106 |
| 1-47 | Me | Me | 4-$O(CH_2)_4CH_3$ | 3-$CF_3$-2-pyridyl | |
| 1-48 | Me | Me | 4-$O(CH_2)_5CH_3$ | 3-$CF_3$-2-pyridyl | 77-79 |
| 1-49 | Me | Me | 2-Me-3-OBu(n) | 3-$CF_3$-2-pyridyl | viscous |
| 1-50 | Me | Me | 4-$O(CH_2)_6CH_3$ | 3-$CF_3$-2-pyridyl | |
| 1-51 | Me | Me | 4-$(CH_2)_6CH_3$ | 3-$CF_3$-2-pyridyl | |
| 1-52 | Me | Me | 4-$O(CH_2)_7CH_3$ | 3-$CF_3$-2-pyridyl | |
| 1-53 | Me | Me | 4-$O(CH_2)_8CH_3$ | 3-$CF_3$-2-pyridyl | |
| 1-54 | Me | Me | 4-$O(CH_2)_9CH_3$ | 3-$CF_3$-2-pyridyl | |
| 1-55 | Me | Me | 4-$O(CH_2)_{10}CH_3$ | 3-$CF_3$-2-pyridyl | |
| 1-56 | Me | Me | 4-$O(CH_2)_{11}CH_3$ | 3-$CF_3$-2-pyridyl | |
| 1-57 | Me | Me | 3-Me-4-OBu(n) | 3-$CF_3$-2-pyridyl | |
| 1-58 | Me | Me | 4-OBu(i) | 3-$CF_3$-2-pyridyl | 116-118 |
| 1-59 | Me | Me | 3-Me-4-OPr(i) | 3-$CF_3$-2-pyridyl | |
| 1-60 | Me | Me | 2-Me-3-OPr(i) | 3-$CF_3$-2-pyridyl | |
| 1-61 | Me | Me | 4-Cl | 3-$CF_3$-2-pyridyl | 116-118 |
| 1-62 | Me | Me | 2-Me-4-$OCHF_2$ | 3-$CF_3$-2-pyridyl | viscous |
| 1-63 | Me | Me | 4-$OSO_2Me$ | 3-$CF_3$-2-pyridyl | 174-176 |
| 1-64 | Me | Me | 4-OPh | 3-$CF_3$-2-pyridyl | viscous |
| 1-65 | Me | Me | 4-Cyclohexyloxy | 3-$CF_3$-2-pyridyl | viscous |
| 1-66 | Me | Me | 4-$OCH(CH_2CH_2CH_3)_2$ | 3-$CF_3$-2-pyridyl | 125-126 |
| 1-67 | Me | Me | 4-$OCH(CH_3)CH_2CH_2CH_3$ | 3-$CF_3$-2-pyridyl | 89-92 |
| 1-68 | Me | Me | 4-$(CH_2)_4CH_3$ | 3-$CF_3$-2-pyridyl | 101-107 |
| 1-69 | Me | Me | 2-Me-3-$O(CH_2)_5CH_3$ | 3-$CF_3$-2-pyridyl | viscous |
| 1-70 | Me | Me | 4-$O(CH_2)_2OCH_3$ | 3-$CF_3$-2-pyridyl | 101-103 |

TABLE 1-continued

| No. | R¹ | R² | X | B | Physical property (melting point °C.) |
|---|---|---|---|---|---|
| 1-71 | Me | Me | 4-OH | 3-CF$_3$-2-pyridyl | 238-240 |
| 1-72 | Me | Me | 4-Cyclopentyloxy | 3-CF$_3$-2-pyridyl | 132-134 |
| 1-73 | Me | Me | 4-OCH$_2$Ph | 3-CF$_3$-2-pyridyl | 142-145 |
| 1-74 | Et | Et | 4-OPr(i) | 3-CF$_3$-2-pyridyl | 130-133 |
| 1-75 | Me | Et | 4-OPr(i) | 3-CF$_3$-2-pyridyl | 112-114 |
| 1-76 | Me | Me | 4-(3-Hexyloxy) | 3-CF$_3$-2-pyridyl | 105-106 |
| 1-77 | Me | Me | 4-(2-Hexyloxy) | 3-CF$_3$-2-pyridyl | 107-111 |
| 1-78 | Me | Me | 2-Me-4-(2-Pentyloxy) | 3-CF$_3$-2-pyridyl | viscous |
| 1-79 | Me | Me | 4-(3-Pentyloxy) | 3-CF$_3$-2-pyridyl | 106-108 |
| 1-80 | Me | Me | 4-OCH$_2$CH(CH$_3$)CH$_2$CH$_3$ | 3-CF$_3$-2-pyridyl | 102-105 |
| 1-81 | Me | Me | 4-OCH$_2$CH$_2$CH(CH$_3$)CH$_3$ | 3-CF$_3$-2-pyridyl | viscous |
| 1-82 | Me | Me | 2-Me-4-OMe | 2-Cl-3-pyridyl | |
| 1-83 | Me | Me | 2-Me-4-OEt | 2-Cl-3-pyridyl | |
| 1-84 | Me | Me | 2-Me-4-OPr | 2-Cl-3-pyridyl | |
| 1-85 | Me | Me | 2-Me-4-OBu | 2-Cl-3-pyridyl | |
| 1-86 | Me | Me | 2-Me-4-OBu(sec) | 2-Cl-3-pyridyl | |
| 1-87 | Me | Me | 2-Me-4-OBu(i) | 2-Cl-3-pyridyl | |
| 1-88 | Me | Me | 2-Me-4-Heptyloxy | 2-Cl-3-pyridyl | |
| 1-89 | Me | Me | 2-Me-4-(2-Heptyloxy) | 2-Cl-3-pyridyl | |
| 1-90 | Me | Me | 2-Me-4-(3-Heptyloxy) | 2-Cl-3-pyridyl | |
| 1-91 | Me | Me | 4-OMe | 2-Cl-3-pyridyl | |
| 1-92 | Me | Me | 4-OEt | 2-Cl-3-pyridyl | |
| 1-93 | Me | Me | 4-OPr | 2-Cl-3-pyridyl | |
| 1-94 | Me | Me | 4-OPr(i) | 2-Cl-3-pyridyl | |
| 1-95 | Me | Me | 4-OBu | 2-Cl-3-pyridyl | |
| 1-96 | Me | Me | 4-OBu(sec) | 2-Cl-3-pyridyl | |
| 1-97 | Me | Me | 4-OBu(i) | 2-Cl-3-pyridyl | |
| 1-98 | Me | Me | 4-Heptyloxy | 2-Cl-3-pyridyl | |
| 1-99 | Me | Me | 4-(2-Heptyloxy) | 2-Cl-3-pyridyl | viscous |
| 1-100 | Me | Me | 4-(3-Heptyloxy) | 2-Cl-3-pyridyl | viscous |
| 1-101 | Me | Me | 2-Me-4-OBu(i) | 3-CF$_3$-2-pyridyl | |
| 1-102 | Me | Me | 2-Me-4-Pentyloxy | 3-CF$_3$-2-pyridyl | |
| 1-103 | Me | Me | 2-Me-4-(3-Pentyloxy) | 3-CF$_3$-2-pyridyl | |
| 1-104 | Me | Me | 2-Me-4-Hexyloxy | 3-CF$_3$-2-pyridyl | |
| 1-105 | Me | Me | 2-Me-4-(2-Hexyloxy) | 3-CF$_3$-2-pyridyl | viscous |
| 1-106 | Me | Me | 2-Me-4-(3-Hexyloxy) | 3-CF$_3$-2-pyridyl | viscous |
| 1-107 | Me | Me | 2-Me-4-Heptyloxy | 3-CF$_3$-2-pyridyl | |
| 1-108 | Me | Me | 2-Me-4-(2-Heptyloxy) | 3-CF$_3$-2-pyridyl | |
| 1-109 | Me | Me | 2-Me-4-(3-Heptyloxy) | 3-CF$_3$-2-pyridyl | |
| 1-110 | Me | Me | 2-Me-4-(4-Heptyloxy) | 3-CF$_3$-2-pyridyl | |
| 1-111 | Me | Me | 2-Me-4-(2-Octyloxy) | 3-CF$_3$-2-pyridyl | |
| 1-112 | Me | Me | 2-Me-4-(2-Nonyloxy) | 3-CF$_3$-2-pyridyl | |
| 1-113 | Me | Me | 4-Pentyloxy | 3-CF$_3$-2-pyridyl | viscous |
| 1-114 | Me | Me | 4-O(CH$_2$)$_3$CH(CH$_3$)CH$_3$ | 3-CF$_3$-2-pyridyl | |
| 1-115 | Me | Me | 4-O(CH$_2$)$_2$CH(CH$_3$)CH$_2$CH$_3$ | 3-CF$_3$-2-pyridyl | |
| 1-116 | Me | Me | 4-OCH$_2$CH(CH$_3$)CH$_2$CH$_2$CH$_3$ | 3-CF$_3$-2-pyridyl | |
| 1-117 | Me | Me | 4-OCH$_2$CH(CH$_2$CH$_3$)CH$_2$CH$_3$ | 3-CF$_3$-2-pyridyl | |
| 1-118 | Me | Me | 4-Heptyloxy | 3-CF$_3$-2-pyridyl | |
| 1-119 | Me | Me | 4-(2-Heptyloxy) | 3-CF$_3$-2-pyridyl | 99-101 |
| 1-120 | Me | Me | 4-(3-Heptyloxy) | 3-CF$_3$-2-pyridyl | 111-115 |
| 1-121 | Me | Me | 4-Octyloxy | 3-CF$_3$-2-pyridyl | |
| 1-122 | Me | Me | 4-(2-Octyloxy) | 3-CF$_3$-2-pyridyl | 100-101 |
| 1-123 | Me | Me | 4-(3-Octyloxy) | 3-CF$_3$-2-pyridyl | |
| 1-124 | Me | Me | 4-(4-Octyloxy) | 3-CF$_3$-2-pyridyl | |
| 1-125 | Me | Me | 4-Nonyloxy | 3-CF$_3$-2-pyridyl | |
| 1-126 | Me | Me | 4-(2-Nonyloxy) | 3-CF$_3$-2-pyridyl | |
| 1-127 | Me | Me | 4-(3-Nonyloxy) | 3-CF$_3$-2-pyridyl | |
| 1-128 | Me | Me | 4-(4-Nonyloxy) | 3-CF$_3$-2-pyridyl | |
| 1-129 | Me | Me | 4-(5-Nonyloxy) | 3-CF$_3$-2-pyridyl | |
| 1-130 | Me | Me | 3-OH | 3-CF$_3$-2-pyridyl | viscous |
| 1-131 | Me | Me | 3-OPr(i) | 3-CF$_3$-2-pyridyl | viscous |
| 1-132 | Me | Me | 3-OBu | 3-CF$_3$-2-pyridyl | 81-83 |
| 1-133 | Me | Me | 3-OBu(sec) | 3-CF$_3$-2-pyridyl | viscous |
| 1-134 | Me | Me | 3-OBu(i) | 3-CF$_3$-2-pyridyl | |
| 1-135 | Me | Me | 3-Pentyloxy | 3-CF$_3$-2-pyridyl | |
| 1-136 | Me | Me | 3-(2-Pentyloxy) | 3-CF$_3$-2-pyridyl | viscous |

TABLE 1-continued

[Structure: X-substituted phenyl ring (positions labeled 2,3,4,5,6) with C1 attached to C(=O)-C(R¹)(R²)-NH-C(=O)-B]

| No. | R¹ | R² | X | B | Physical property (melting point ° C.) |
|---|---|---|---|---|---|
| 1-137 | Me | Me | 3-(3-Pentyloxy) | 3-CF₃-2-pyridyl | |
| 1-138 | Me | Me | 3-(2-Hexyloxy) | 3-CF₃-2-pyridyl | |
| 1-139 | Me | Me | 3-(3-Hexyloxy) | 3-CF₃-2-pyridyl | |
| 1-140 | Me | Me | 3-Heptyloxy | 3-CF₃-2-pyridyl | |
| 1-141 | Me | Me | 3-(2-Heptyloxy) | 3-CF₃-2-pyridyl | |
| 1-142 | Me | Me | 3-(3-Heptyloxy) | 3-CF₃-2-pyridyl | |
| 1-143 | Me | Me | 3-(4-Heptyloxy) | 3-CF₃-2-pyridyl | |
| 1-144 | Me | Me | 3-(2-Octyloxy) | 3-CF₃-2-pyridyl | |
| 1-145 | Me | Me | 3-(2-Nonyloxy) | 3-CF₃-2-pyridyl | |
| 1-146 | Me | Me | 4-CH₂OCH₃ | 3-CF₃-2-pyridyl | |
| 1-147 | Me | Me | 4-CH₂OCH₂CH₃ | 3-CF₃-2-pyridyl | |
| 1-148 | Me | Me | 4-CH₂OCH(CH₃)₂ | 3-CF₃-2-pyridyl | 100-102 |
| 1-149 | Me | Me | 4-CH₂OCH₂CF₃ | 3-CF₃-2-pyridyl | |
| 1-150 | Me | Me | 4-CH₂SCH₂CH₃ | 3-CF₃-2-pyridyl | |

TABLE 2

[Structure: A-C(=O)-C(R¹)(R²)-NH-C(=O)-B]

| No. | A | R¹ | R² | B | Physical property (melting point ° C.) |
|---|---|---|---|---|---|
| 2-1 | 2,2-difluoro-4-methyl-5-methyl-benzo[1,3]dioxole | Me | Me | 3-CF₃-2-pyridyl | 130-134 |
| 2-2 | 2,2,3,3-tetrafluoro-5-methyl-6-methyl-1,4-benzodioxine | Me | Me | 3-CF₃-2-pyridyl | 140-142 |
| 2-3 | 2,2-difluoro-5-methyl-benzo[1,3]dioxole | Me | Me | 3-CF₃-2-pyridyl | |
| 2-4 | 2,2,3,3-tetrafluoro-6-methyl-1,4-benzodioxine | Me | Me | 3-CF₃-2-pyridyl | |
| 2-5 | 2,2-difluoro-4-methyl-benzo[1,3]dioxole | Me | Me | 3-CF₃-2-pyridyl | |
| 2-6 | 4-methyl-benzo[1,3]dioxole | Me | Me | 3-CF₃-2-pyridyl | 149-151 |
| 2-7 | 2,2-dimethyl-4-methyl-5-methyl-benzo[1,3]dioxole | Me | Me | 3-CF₃-2-pyridyl | |
| 2-8 | 4-methyl-5-methyl-benzo[1,3]dioxole | Me | Me | 3-CF₃-2-pyridyl | |

TABLE 3

| No. | ¹H-NMR δ ppm (Solvent: CDCl₃/400 MHz) |
|---|---|
| 1-13 | 1.76 (s, 6H), 2.33 (s, 3H), 7.25 (d, 1H), 7.64 (dd, 1H), 7.76 (dd, 1H), 7.88 (d, 1H), 8.06 (d, 1H), 8.20 (s, 1H), 8.71 (d, 1H) |
| 1-49 | 0.93 (t, 3H), 1.47 (m, 2H), 1.74 (m, 2H), 1.84 (s, 6H), 3.96 (t, 2H), 6.73 (d, 1H), 7.51 (dd, 1H), 7.91 (m, 2H), 8.05 (d, 1H), 8.48 (s, 1H), 8.72 (d, 1H) |

TABLE 3-continued

| No. | $^1$H-NMR δ ppm (Solvent: CDCl$_3$/400 MHz) |
|---|---|
| 1-62 | 1.77 (s, 6H), 2.38 (s, 3H), 6.46 (t, 1H), 6.84 (dd, 1H), 6.96 (s, 1H), 7.48 (d, 1H), 7.53 (dd, 1H), 8.10 (d, 1H), 8.25 (s, 1H), 8.71 (d, 1H) |
| 1-64 | 1.82 (s, 6H), 6.92 (d, 2H), 7.01 (d, 2H), 7.14 (t, 1H), 7.34 (m, 2H), 7.54 (dd, 1H), 8.03 (d, 2H), 8.08 (d, 1H), 8.72 (d, 1H) |
| 1-65 | 1.33 (m, 2H), 1.51 (m, 2H), 1.76 (m, 6H), 1.87 (s, 6H), 4.30 (m, 1H), 6.82 (d, 2H), 7.52 (dd, 1H), 8.01 (d, 2H), 8.08 (d, 1H), 8.49 (s, 1H), 8.73 (d, 1H) |
| 1-69 | 0.91 (t, 3H), 1.35 (m, 4H), 1.47 (m, 2H), 1.80 (m, 2H), 1.87 (s, 6H), 2.23 (s, 3H), 4.0 (t, 2H), 6.78 (d, 1H), 7.54 (dd, 1H), 7.89 (d, 1H), 7.93 (dd, 1H), 8.10 (d, 1H), 8.48 (s, 1H), 8.75 (d, 1H) |
| 1-78 | 0.90 (t, 3H), 1.24 (d, 3H), 1.47 (m, 4H), 1.78 (s, 6H), 4.36 (m, 1H), 6.58 (dd, 1H), 6.72 (d, 1H), 7.44 (d, 1H), 7.51 (dd, 1H), 8.08 (d, 1H), 8.39 (s, 1H), 8.71 (d, 1H) |
| 1-81 | 0.93 (d, 6H), 1.66 (q, 2H), 1.82 (m, 1H), 1.86 (s, 6H), 4.01 (t, 2H), 6.85 (d, 2H), 7.54 (dd, 1H), 8.06 (d, 2H), 8.10 (d, 1H), 8.48 (s, 1H), 8.75 (d, 1H) |
| 1-99 | 0.88 (t, 3H), 1.29 (d, 3H), 1.34 (m, 6H), 1.54 (m, 1H), 1.73 (m, 1H), 1.87 (s, 6H), 4.43 (m, 1H), 6.86 (d, 2H), 7.29 (dd, 1H), 7.70 (s, 1H), 7.91 (dd, 1H), 8.04 (d, 2H), 8.43 (dd, 1H) |
| 1-100 | 0.88 (t, 3H), 0.94 (t, 3H), 1.32 (m, 4H), 1.68 (m, 4H), 1.87 (s, 6H), 4.25 (m, 1H), 6.87 (d, 2H), 7.28 (dd, 1H), 7.70 (s, 1H), 7.90 (dd, 1H), 8.03 (d, 2H), 8.43 (dd, 1H) |
| 1-105 | 0.89 (t, 3H), 1.27 (d, 3H), 1.33 (m, 4H), 1.55 (m, 1H), 1.73 (m, 1H), 1.82 (s, 6H), 2.37 (s, 3H), 4.36 (m, 1H), 6.61 (dd, 1H), 6.74 (d, 1H), 7.47 (d, 1H), 7.55 (dd, 1H), 8.11 (dd, 1H), 8.41 (s, 1H), 8.74 (dd, 1H) |
| 1-106 | 0.91 (t, 3H), 0.92 (t, 3H), 1.39 (m, 4H), 1.63 (m, 4H), 1.88 (s, 6H), 2.37 (s, 3H), 4.19 (m, 1H), 6.61 (dd, 1H), 6.74 (d, 1H), 7.46 (d, 1H), 7.54 (dd, 1H), 8.11 (dd, 1H), 8.42 (s, 1H), 8.74 (dd, 1H) |
| 1-113 | 0.90 (t, 3H), 1.36 (m, 4H), 1.74 (m, 2H), 1.85 (s, 6H), 3.96 (t, 2H), 6.83 (m, 2H), 7.53 (dd, 1H), 8.05 (m, 2H), 8.10 (d, 1H), 8.48 (s, 1H), 8.74 (d, 1H) |
| 1-130 | 1.78 (s, 6H), 6.93 (dd, 1H), 7.18 (t, 1H), 7.51 (d, 1H), 7.55 (m, 2H), 8.11 (d, 1H), 8.32 (s, 1H), 8.72 (d, 1H) |
| 1-131 | 1.28 (d, 6H), 1.82 (s, 6H), 4.55 (m, 1H), 6.97 (dd, 1H), 7.21 (d, 1H), 7.47 (d, 1H), 7.53 (m, 2H), 8.10 (d, 1H), 8.73 (d, 1H) |
| 1-133 | 0.87 (m, 3H), 1.19 (m, 3H), 1.38 (s, 6H), 1.52 (s, 6H), 1.61 (m, 2H), 4.21 (m, 1H), 6.77 (dd, 1H), 6.89 (m, 2H), 7.16 (t, 1H), 7.53 (m, 1H), 7.61 (t, 1H), 8.15 (d, 1H) |
| 1-136 | 0.88 (t, 3H), 1.22 (d, 3H), 1.38 (s, 6H), 4.36 (m, 1H), 6.96 (dd, 1H), 7.21 (t, 1H), 7.47 (d, 1H), 7.52 (m, 2H), 8.09 (d, 1H), 8.36 (s, 1H), 8.72 (d, 1H) |

Now, Test Examples for the composition of the present invention will be described. In each test, the controlling index was determined on the basis of the following standards:
[Controlling index]:[Degree of disease outbreak:Visual observation]
5: No lesions nor sporulation recognizable
4: Length of lesions, number of lesions or area of sporulation is less than 10% of non-treated plot
3: Length of lesions, number of lesions or area of sporulation is less than 40% of non-treated plot
2: Length of lesions, number of lesions or area of sporulation is less than 70% of non-treated plot
1: Length of lesions, number of lesions or area of sporulation is at least 70% of non-treated plot Test Example 1

Test on Preventive Effect Against Wheat Powdery Mildew

Wheat (cultivar: Norin-61-go) was cultivated in a plastic pot having a diameter of 7.5 cm, and when it reached 1.5-leaf stage, 10 ml of a chemical solution having the carboxylic acid amide derivative of the formula (I) or a salt thereof adjusted to a prescribed concentration, was applied by a spray gun. After the chemical solution dried (the same day as the application), conidia of *Erysiphe graminis* were dusted and inoculated and maintained in a constant temperature chamber at 20° C. From 6 to 7 days after the inoculation, the area of sporulation was investigated, and the controlling index was determined in accordance with the above evaluation standards. The test was carried out with respect to the above compounds No. 1-1, 1-2, 1-3, 1-4, 1-5, 1-6, 1-7, 1-9, 1-12, 1-20, 1-22, 1-24, 1-46, 1-48, 1-67, 1-75, 1-76, 1-78, 1-80, 1-132 and 2-1 and all compounds showed effects with a controlling index of 4 or 5 at a concentration of 500 ppm.

For the purpose of comparison, the test was carried out with respect to compound No. 1-52 disclosed in JP-A-2005-179234 i.e. 3-fluoro-N-(2-methyl-1-oxo-1-(4'-(trifluoromethoxy)biphenyl-4-yl)propan-2-yl)isonicotinamide (hereinafter referred to as Comparative Compound 1), whereby the controlling index at 500 ppm was 1.

Test Example 2

Test on Preventive Effect Against Cucumber Powdery Mildew

Cucumber (cultivar: Sagamihanpaku) was cultivated in a plastic pot having a diameter of 7.5 cm, and when it reached 1.5-leaf stage, 10 ml of a chemical solution having the carboxylic acid amide derivative of the formula (I) or a salt thereof adjusted to a prescribed concentration, was applied by a spray gun. After the chemical solution dried (the same day as the application or the next day), a suspension of conidia of *Sphaerotheca fuliginea* was sprayed and inoculated and maintained in a constant temperature chamber at 20° C. From 6 to 7 days after the inoculation, the area of sporulation was investigated, and the controlling index was determined in accordance with the above evaluation standards. The test was carried out with respect to the above compounds No. 1-1, 1-2, 1-3, 1-4, 1-5, 1-6, 1-7, 1-8, 1-9, 1-10, 1-11, 1-12, 1-13, 1-14, 1-15, 1-16, 1-17, 1-20, 1-22, 1-23, 1-43, 1-46, 1-48, 1-58, 1-65, 1-66, 1-67, 1-74, 1-75, 1-76, 1-77, 1-78, 1-79, 1-80, 1-81, 1-120, 1-122, 1-131, 1-136 and 2-1 and all compounds showed effects with a controlling index of 4 or 5 at a concentration of 500 ppm.

Test Example 3

Test on Preventive Effect Against Rice Blast

Rice (cultivar: Nihonbare) was cultivated in a plastic pot having a diameter of 7.5 cm, and when it reached 1.5-leaf stage, 10 ml of a chemical solution having the carboxylic acid amide derivative of the formula (I) or a salt thereof adjusted to a prescribed concentration, was applied by a spray gun. After the chemical solution dried (the same day as the application or the next day), a suspension of conidia of *Pyricularia oryzae* was sprayed and inoculated and maintained in an inoculation box at 20° C. for 24 to 96 hours and thereafter maintained in a constant temperature chamber at 20° C. From 5 to 7 days after the inoculation, the number of lesions were investigated, and the controlling index was determined in accordance with the above evaluation standards. The test was carried out with respect to the above compounds No. 1-2 and 1-20 and all compounds showed effects with a controlling index of 4 or 5 at a concentration of 500 ppm.

Test Example 4

Test on Preventive Effect Against Kidney Bean Stem Rot

Kidney bean (cultivar: Taisyou Kintoki) was cultivated in a plastic pot having a diameter of 15 cm, and when the main leaf developed sufficiently, 10 ml of a chemical solution having the carboxylic acid amide derivative of the formula (I) or a salt thereof adjusted to a prescribed concentration, was applied by a spray gun. After the chemical solution dried (the same day as the application or the next day), mycelial disc of *Sclerotinia sclerotiorum* was inoculated and maintained in a constant temperature chamber at 20° C. Three days after the inoculation, the length of lesions (mm) was investigated, and the controlling index was determined in accordance with the above evaluation standards. The test was carried out with respect to the above compounds No. 1-1, 1-2, 1-11, 1-17, 1-18, 1-34, 1-43, 1-49, 1-58, 1-65, 1-66, 1-68, 1-69, 1-70, 1-74, 1-77, 1-79, 1-99, 1-100, 1-105, 1-106, 1-113, 1-119, 1-120, 1-122, 1-131 and 1-136 and all compounds showed effects with a controlling index of 4 or 5 at a concentration of 500 ppm.

Test Example 5

Test on Preventive Effect Against Wheat Glume Blotch

Wheat (cultivar: Norin-61-go) was cultivated in a plastic pot having a diameter of 7.5 cm, and when it reached 1.5-leaf stage, 10 ml of a chemical solution having the carboxylic acid amide derivative of the formula (I) or a salt thereof adjusted to a prescribed concentration, was applied by a spray gun. After the chemical solution dried (the same day as the application), a suspension of conidia of *Septoria nodorum* was sprayed and inoculated and maintained in an inoculation box at 20° C. for 72 to 96 hours and thereafter maintained in a constant temperature chamber at 20° C. From 5 to 10 days after the inoculation, the number of lesions was investigated, and the controlling index was determined in accordance with the above evaluation standards. The test was carried out with respect to the above compounds No. 1-13, 1-14, 1-61, 1-62, 1-64 and 1-72, and all compounds showed effects with a controlling index of 4 or 5 at a concentration of 500 ppm.

Test Example 6

Test on Preventive Effect Against Kidney Bean Gray Mold

Kidney bean (cultivar: Taisyou Kintoki) was cultivated in a plastic pot having a diameter of 15 cm, and when the main leaf developed sufficiently, 10 ml of a chemical solution having the carboxylic acid amide derivative of the formula (I) or a salt thereof adjusted to a prescribed concentration, was applied by a spray gun. After the chemical solution dried (the next day as the application), a suspension of spores of *Botrytis cinerea* (potato-glucose extract diluted to 50% with water) was inoculated and maintained in a constant temperature chamber at 20° C. From 3 to 4 days after the inoculation, the length of lesions (mm) was investigated, and the controlling index was determined in accordance with the above evaluation standards. The test was carried out with respect to the above compounds No. 1-1, 1-2, 1-7, 1-8, 1-10, 1-15, 1-16, 1-18, 1-34, 1-49, 1-61, 1-62, 1-64, 1-68, 1-69, 1-70, 1-72, 1-81, 1-99, 1-100, 1-105, 1-106, 1-113 and 1-119 and all compounds showed effects with a controlling index of 4 at a concentration of 500 ppm.

For the purpose of comparison, the test was carried out with respect to Comparative Compound 1, whereby the controlling index at 500 ppm was 1.

Now, Formulation Examples of the composition of the present invention will be described below. However, the weight ratio, type of formulation or the like is by no means restricted to the following Examples.

Formulation Example 1

| | |
|---|---|
| (1) Compound of the formula (I) | 20 parts by weight |
| (2) Clay | 72 parts by weight |
| (3) Sodium lignin sulfonate | 8 parts by weight |

The above components are uniformly mixed to obtain a wettable powder.

Formulation Example 2

| | |
|---|---|
| (1) Compound of the formula (I) | 5 parts by weight |
| (2) Talc | 95 parts by weight |

The above components are uniformly mixed to obtain a dust.

Formulation Example 3

| | |
|---|---|
| (1) Compound of the formula (I) | 20 parts by weight |
| (2) N,N'-dimethylacetamide | 20 parts by weight |
| (3) Polyoxyethylene alkyl phenyl ether | 10 parts by weight |
| (4) Xylene | 50 parts by weight |

The above components are uniformly mixed and dissolved to obtain an emulsifiable concentrate.

Formulation Example 4

| | |
|---|---|
| (1) Clay | 68 parts by weight |
| (2) Sodium lignin sulfonate | 2 parts by weight |
| (3) Polyoxyethylene alkyl aryl sulfate | 5 parts by weight |
| (4) Fine silica | 25 parts by weight |

A mixture of the above components and the compound of the formula (I) are mixed in a weight ratio of 4:1 to obtain a wettable powder.

Formulation Example 5

| | |
|---|---|
| (1) Compound of the formula (I) | 50 parts by weight |
| (2) Oxylated polyalkylphenyl phosphate-triethanolamine | 2 parts by weight |

-continued

| (3) Silicone | 0.2 part by weight |
| (4) Water | 47.8 parts by weight |

The above components are uniformly mixed and pulverized to obtain a stock solution, and

| (5) Sodium polycarboxylate | 5 parts by weight |
| (6) Anhydrous sodium sulfate | 42.8 parts by weight | are further added thereto, followed by uniform mixing, granulation and drying to obtain a water-dispersible granules.

Formulation Example 6

| (1) Compound of the formula (I) | 5 parts by weight |
| (2) Polyoxyethylene octylphenyl ether | 1 part by weight |
| (3) Phosphate of polyoxyethylene | 0.1 part by weight |
| (4) Particulate calcium carbonate | 93.9 parts by weight |

The above components (1) to (3) are preliminarily mixed uniformly and diluted with a proper amount of acetone, the diluted mixture is sprayed on the component (4), and acetone is removed to obtain granules.

Formulation Example 7

| (1) Compound of the formula (I) | 2.5 parts by weight |
| (2) N-methyl-2-pyrrolidone | 2.5 parts by weight |
| (3) Soybean oil | 95.0 parts by weight |

The above components are uniformly mixed and dissolved to obtain an ultra low volume formulation.

Formulation Example 8

| (1) Compound of the formula (I) | 20 parts by weight |
| (2) Oxylated polyalkylphenyl phosphate triethanolamine | 2 parts by weight |
| (3) Silicone | 0.2 part by weight |
| (4) Xanthan gum | 0.1 part by weight |
| (5) Ethylene glycol | 5 parts by weight |
| (6) Water | 72.7 parts by weight |

The above components are uniformly mixed and pulverized to obtain a water-based suspension concentrate.

The invention claimed is:

1. A fungicidal composition containing a carboxylic acid amide derivative of the formula (I) or a salt thereof as an active ingredient:

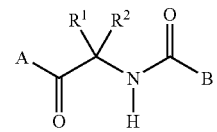

(I)

wherein
A is phenyl which is optionally substituted by X,
B is 2-pyridyl which is optionally substituted with halogen, alkyl, haloalkyl, alkoxy, or haloalkoxy;
each of $R^1$ and $R^2$ is alkyl, or $R^1$ and $R^2$ may together form a 3- to 6-membered saturated carbon ring;
X is halogen, alkyl, haloalkyl, alkenyl, haloalkenyl, alkynyl, haloalkynyl, hydroxy, alkoxy, haloalkoxy, alkenyloxy, haloalkenyloxy, alkynyloxy, haloalkynyloxy, cycloalkyloxy, alkylthio, haloalkylthio, alkenylthio, haloalkenylthio, alkynylthio, haloalkynylthio, alkylsulfonyloxy, haloalkylsulfonyloxy, alkoxyalkoxy, haloalkoxyalkoxy, alkoxyhaloalkoxy, haloalkoxyhaloalkoxy, alkoxyalkyl, haloalkoxyalkyl, alkylthioalkyl, haloalkylthioalkyl, phenyl which is optionally substituted by Y, phenoxy which is optionally substituted by Y, benzyloxy which is optionally substituted Y, pyridyl which is optionally substituted by Y, or pyridyloxy which is optionally substituted by Y; and
Y is halogen, alkyl, haloalkyl, alkenyl, haloalkenyl, alkynyl, haloalkynyl, alkoxy or haloalkoxy.

2. The fungicidal composition according to claim 1, wherein A is phenyl which is optionally substituted by X; B is 2-pyridyl which is optionally substituted with halogen, alkyl, haloalkyl, alkoxy, or haloalkoxy; each of $R^1$ and $R^2$ is alkyl, or $R^1$ and $R^2$ may together form a 3- to 6-membered saturated carbon ring; X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, phenyl substituted by Y, phenoxy substituted by Y, pyridyl substituted by Y, or pyridyloxy substituted by Y; and Y is halogen, alkyl, haloalkyl, alkenyl, haloalkenyl, alkynyl, haloalkynyl or alkoxy.

3. The fungicidal composition according to claim 2, wherein A is phenyl substituted by halogen, alkyl or alkoxy; B is 2-pyridyl substituted by halogen, alkyl or haloalkyl; and each of $R^1$ and $R^2$ is alkyl.

4. The fungicidal composition according to claim 3, wherein A is phenyl substituted by at least two substituents selected from the group consisting of halogen, alkyl and alkoxy.

5. A carboxylic acid amide derivative of the formula (I) or a salt thereof, as defined in claim 1.

6. A carboxylic acid amide derivative of the formula (I-a) or a salt thereof:

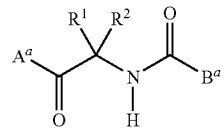

(I-a)

wherein $A^a$ is phenyl which is optionally substituted by X, $B^a$ is 2-pyridyl which is optionally substituted with halogen, alkyl, haloalkyl, alkoxy, or haloalkoxy; each of $R^1$ and $R^2$ is alkyl, or $R^1$ and $R^2$ optionally together form a 3- to 6-membered saturated carbon ring; X is halogen, alkyl, haloalkyl, alkenyl, haloalkenyl, alkynyl, haloalkynyl, hydroxy, alkoxy, haloalkoxy, alkenyloxy, haloalkenyloxy, alkynyloxy, haloalkynyloxy, cycloalkyloxy, alkylthio, haloalkylthio, alkenylthio, haloalkenylthio, alkynylthio, haloalkynylthio, alkylsulfonyloxy, haloalkylsulfonyloxy, alkoxyalkoxy, haloalkoxyalkoxy, alkoxyhaloalkoxy, haloalkoxyhaloalkoxy, alkoxyalkyl, haloalkoxyalkyl, alkylthioalkyl, haloalkylthioalkyl, phenyl which is optionally substituted by Y, phenoxy which is optionally substituted by Y, benzyloxy which is optionally substituted by Y, pyridyl which is optionally substituted by Y, or pyridyloxy which is optionally substituted by Y; and Y is halogen, alkyl, haloalkyl, alkenyl, haloalkenyl, alkynyl, haloalkynyl, alkoxy or haloalkoxy.

7. The carboxylic acid amide derivative or a salt thereof according to claim 6, wherein $A^a$ is phenyl substituted by halogen, alkyl or alkoxy; $B^a$ is 2-pyridyl substituted by halogen, alkyl or haloalkyl; and each of $R^1$ and $R^2$ is alkyl.

8. The carboxylic acid amide derivative or a salt thereof according to claim 7, wherein $A^a$ is phenyl substituted by at least two substituents selected from the group consisting of halogen, alkyl and alkoxy.

9. A mixed fungicidal composition comprising a carboxylic acid amide derivative of the formula (I) or a salt thereof, as defined in claim 1, and another fungicidally active ingredient compound, as active ingredients.

10. The mixed fungicidal composition according to claim 9, wherein said another fungicidally active ingredient compound is at least one member selected from the group consisting of an anilinopyrimidine compound, a pyridinamine compound, an azole compound, a quinoxaline compound, a dithiocarbamate compound, an organic chlorine compound, an imidazole compound, a cyano acetamide compound, a phenylamide compound, a sulfenic acid compound, a copper compound, an isoxazole compound, an organic phosphorus compound, an N-halogenothioalkyl compound, a dicarboxyimide compound, a benzanilide compound, an anilide compound, a piperazine compound, a pyridine compound, a carbinol compound, a piperidine compound, a morpholine compound, an organic tin compound, an urea compound, a cinnamic acid compound, a phenylcarbamate compound, a cyanopyrrole compound, a strobilurin compound, an oxazolidinone compound, a thiazolecarboxamide compound, a silylamide compound, an amino acid amide carbamate compound, an imidazolidine compound, a hydroxyanilide compound, a benzenesulfonamide compound, an oxime ether compound, a phenoxyamide compound, an antibiotic, a guanidine compound, isoprothiolane, pyroquilon, diclomezine, quinoxyfen, propamocarb hydrochloride, spiroxamine, chloropicrin, dazomet, metam-sodium, metrafenone, UBF-307, diclocymet, proquinazid, amisulbrom, KIF-7767, Syngenta 446510 and fluopicolide.

11. A method for controlling noxious fungus, which comprises contacting a plant, soil, or noxious fungus with an effective amount of a carboxylic acid amide derivative of the formula (1) or a salt thereof, as defined in claim 1.

12. The method for controlling noxious fungi according to claim 11, wherein the noxious fungi are at least one of wheat powdery mildew, cucumber powdery mildew, kidney bean stem rot or kidney bean gray mold.

* * * * *